(12) United States Patent
Ayalew et al.

(10) Patent No.: US 7,794,734 B2
(45) Date of Patent: Sep. 14, 2010

(54) *MANNHEIMIA HAEMOLYTICA* CHIMERIC OUTER MEMBRANE PROTEIN PLPE AND LEUKOTOXIN EPITOPES AS A VACCINE OR VACCINE COMPONENT AGAINST SHIPPING FEVER

(75) Inventors: Sahlu Ayalew, Stillwater, OK (US); Anthony W. Confer, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 11/545,069

(22) Filed: Oct. 6, 2006

(65) Prior Publication Data

US 2007/0134272 A1 Jun. 14, 2007

Related U.S. Application Data

(60) Continuation-in-part of application No. 11/235,982, filed on Sep. 27, 2005, now Pat. No. 7,144,580, which is a division of application No. 10/696,544, filed on Oct. 29, 2003, now abandoned.

(60) Provisional application No. 60/757,342, filed on Jan. 9, 2006, provisional application No. 60/422,305, filed on Oct. 30, 2002.

(51) Int. Cl.
*A61K 39/00* (2006.01)
*A61K 39/102* (2006.01)
*A61K 39/02* (2006.01)
*A61K 39/38* (2006.01)
*A61K 39/116* (2006.01)
*A61K 38/00* (2006.01)
*C07K 14/00* (2006.01)

(52) U.S. Cl. ............... 424/255.1; 424/192.1; 424/190.1; 424/184.1; 424/234.1; 424/203.1; 514/2; 530/350; 530/300; 530/825; 530/806

(58) Field of Classification Search .............. 424/192.1, 424/184.1, 203.1, 190.1, 234.1, 255.1; 514/2; 530/350, 300, 825, 806
See application file for complete search history.

(56) References Cited

U.S. PATENT DOCUMENTS

| | | | | |
|---|---|---|---|---|
| 5,055,400 | A | 10/1991 | Lo et al. | 435/69.1 |
| 5,238,823 | A | 8/1993 | Potter et al. | 435/69.2 |
| 5,273,889 | A | 12/1993 | Potter et al. | 435/69.51 |
| 5,476,657 | A | 12/1995 | Potter | 424/184.1 |
| 5,554,372 | A | 9/1996 | Hunter | 424/280.1 |
| 5,594,107 | A | 1/1997 | Potter et al. | 530/350 |
| 5,708,155 | A | 1/1998 | Potter et al. | 536/23.4 |
| 5,723,129 | A | 3/1998 | Potter et al. | 424/200.1 |
| 5,837,268 | A | 11/1998 | Potter et al. | 424/255.1 |
| 5,871,750 | A | 2/1999 | Potter et al. | 424/255.1 |
| 5,932,440 | A * | 8/1999 | Chatterjee et al. | 435/69.1 |
| 6,022,960 | A | 2/2000 | Potter et al. | 536/23.1 |
| 6,096,320 | A | 8/2000 | Potter et al. | 424/255.1 |
| 6,475,754 | B1 | 11/2002 | Bemis et al. | 435/69.1 |
| 6,521,746 | B1 | 2/2003 | Potter et al. | 536/23.1 |
| 6,790,950 | B2 | 9/2004 | Lowery et al. | 536/23.7 |
| 6,797,272 | B1 | 9/2004 | Potter et al. | 536/23.4 |
| 7,144,580 | B2 | 12/2006 | Confer et al. | 424/255.1 |
| 2004/0033234 | A1 | 2/2004 | Berinstein et al. | |
| 2004/0156865 | A1 | 8/2004 | Confer et al. | |
| 2005/0287118 | A1 | 12/2005 | Tian et al. | |
| 2006/0078572 | A1 | 4/2006 | Confer et al. | |

FOREIGN PATENT DOCUMENTS

WO WO 93/21323 10/1993
WO WO 2004/041182 A2 5/2004

OTHER PUBLICATIONS

International Search Report, Oct. 1, 2007.
Pandher, et al., "Genetic and Immunologic Analyses of PlpE, a Lipoprotein Important in Complement-Mediated Killing of *Pasteurella haemolytica* Serotype 1," Infection and Immunity, Dec. 1998, pp. 5613-5619, vol. 66, No. 12, Published in: United States.
Morton, et al., "Vaccination of cattle with outer membrane protein-enriched fractions of *Pasteurella haemolytica* and resistance against experimental challenge exposure," College of Veterinary Medicine and the Agricultural Experiment Station, Jul. 1995, pp. 875-879, vol. 56, No. 7, Publisher: Am J Vet Res, Published in: United States.
Mosier, et al, "*Pasteurella haemolytica* Antigens Associated with Resistance to Pneumonic Pasteurellosis," Infection and Immunity, Mar. 1989, pp. 711-716, vol. 57, No. 3, Published in: United States.
Pandher, et al., "Identification of immunogenic, surface-exposed outer membrane proteins of *Pasteurella haemolytica* serotype 1," Veterinary Microbiology, Nov. 1998, pp. 215-226, vol. 65, Publisher: Elsevier Science B.V., Published in: United States.
Confer, et al., Abstract; "Serum antibody responses of cattle to iron-regulated outer membrane proteins of *Pasteurella haemolytica* A1," Vet Immunol Immunopathol, Jul. 1995, pp. 101-110, vol. 47, No. 1-2, Published in: United States.
Confer, et al., "Immunogenicity of recombinant *Mannheimia haemolytica* serotype 1 outer membrane protein PlpE and augmentation of a commercial vaccine," Vaccine, Feb. 2003, pp. 2821-2829, vol. 21, Publisher: Elsevier Science Ltd., Published in: United States.
Pandher, et al., "Identification of Immunogenic, surface-exposed outer membrane proteins of *Pasteurella haemolytica* serotype 1," Veterinary Microbiology 65 (1999) pp. 215-226.

(Continued)

*Primary Examiner*—S. Devi
(74) *Attorney, Agent, or Firm*—Fellers, Snider, Blankenship, Bailey & Tippens

(57) ABSTRACT

Vaccine preparations for the prevention and treatment of bovine respiratory disease (BRD) and, in particular, its most severe form, termed "shipping fever", are provided. The preparations comprise chimeric proteins comprising immunodominant epitopes of recombinant *Mannheimia haemolytica* outer membrane protein PlpE, and immunodominant epitopes of recombinant *M. haemolytica* leukotoxin.

13 Claims, 26 Drawing Sheets

OTHER PUBLICATIONS

PCT International Search Report issued in connection with PCT/US03/34574, date of Mailing Jun. 18, 2004.

Confer, et al., "Immunogenicity of recombinant *Mannheimia haemolytica* serotype 1 outer membrane protein PlpE and augmentation of a commercial vaccine," Vaccine 21 (2003) pp. 2821-2829.

Lainson, et al., "Characterization of epitopes Involved in the neutralization of *Pasteurella haemolytica* serotype A1 leukotoxin," Microbiology (1996) pp. 2499-2507.

Hughes, et al., "Molecular Chimerization of *Pasteurella haemolytica* Leukotoxin to Interleukin-2: Effects on Cytokine and Antigen Function," Infection and Immunity, (1992) pp. 565-570, vol. 60, No. 2, Publisher: American Society for Microbiology.

Rajeev, et al., "*Bordetella bronchiseptica* fimbrial protein-enhanced immunogenicity of a *Mannheimia haemolytica* leukotixin fragment," Vaccine 19 (2001) pp. 4842-4850, Publisher: Elsevier Science Ltd., Published in: United States.

* cited by examiner

A.

TPNHPKPVLVPKTQNNLQAQNVPQAQNASQAQNAPQAQNAPQAQNAPQVENAPQA

B.

ACACCGAATCACCCCAAACCAGTACTAGTACCAAAAACACAAAATAATCTTCAAGC
ACAAAATGTTCCTCAGGCACAAAATGCCTCTCAGGCACAAAATGCCCCTCAGGCAC
AAAATGCTCCTCAGGCACAAAATGCTCCTCAGGTGGAAAATGCTCCTCAGGCA

SDSNLKDLTFEKVKHNLVITNSKKEKVTIQNWFREADFAKEVPNYKATKDEKIEEIIGQN
GERITSKQVDDLIAKGNGKITQDELSKVVDNYELLKHSKNVTNSLDKLISSVSAFTSSNDS
RNVLVAPTSM

B.

TCTGATTCGAACTTAAAAGATTTAACATTTGAAAAAGTTAAACATAATCTTGTCATC
ACGAATAGCAAAAAGAGAAAGTGACCATTCAAAACTGGTTCCGAGAGGCTGATTT
TGCTAAAGAAGTGCCTAATTATAAAGCAACTAAAGATGAGAAAATCGAAGAAATCA
TCGGTCAAAATGGCGAGCGGATCACCTCAAAGCAAGTTGATGATCTTATCGCAAAA
GGTAACGGCAAAATTACCCAAGATGAGCTATCAAAAGTTGTTGATAACTATGAATTG
CTCAAACATAGCAAAAATGTGACAAACAGCTTAGATAAGTTAATCTCATCTGTAAGT
GCATTTACCTCGTCTAATGATTCGAGAAATGTATTAGTGGCTCCAACTTCAATG

Figure 8 A-B

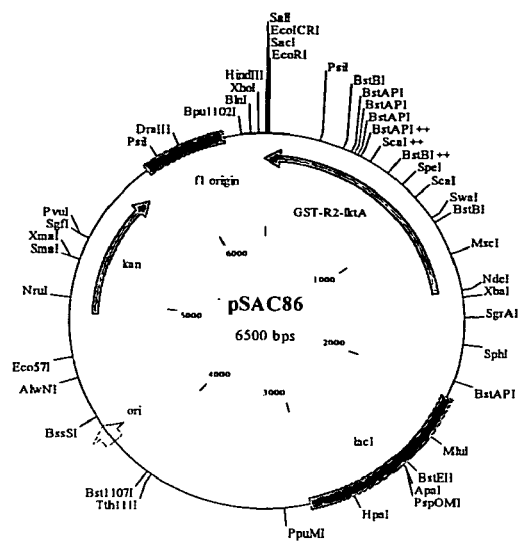
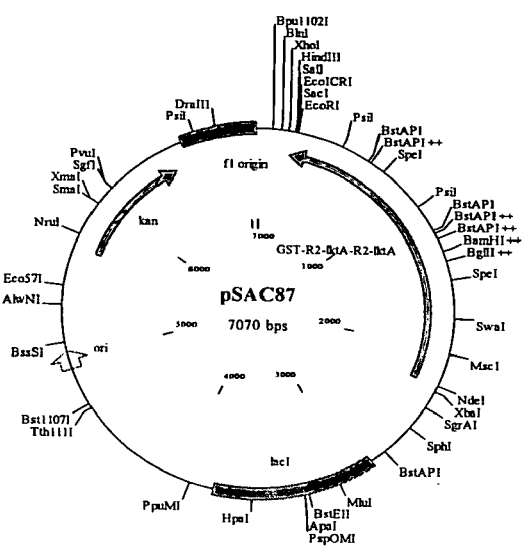
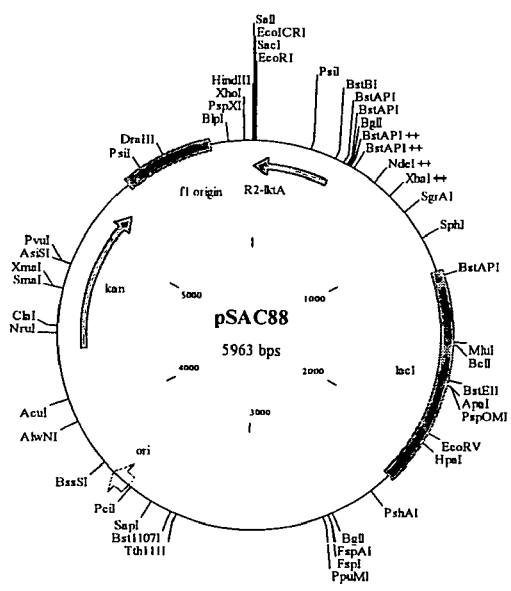
Figure 9 A-C

9D
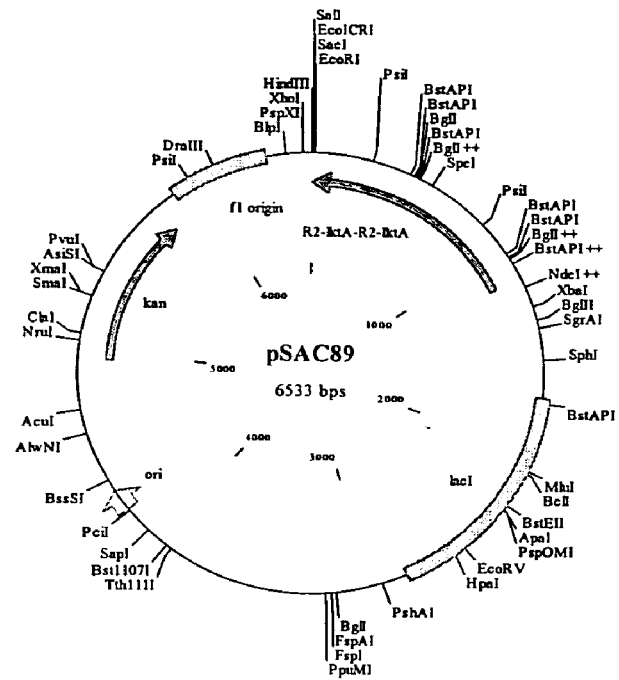
9E
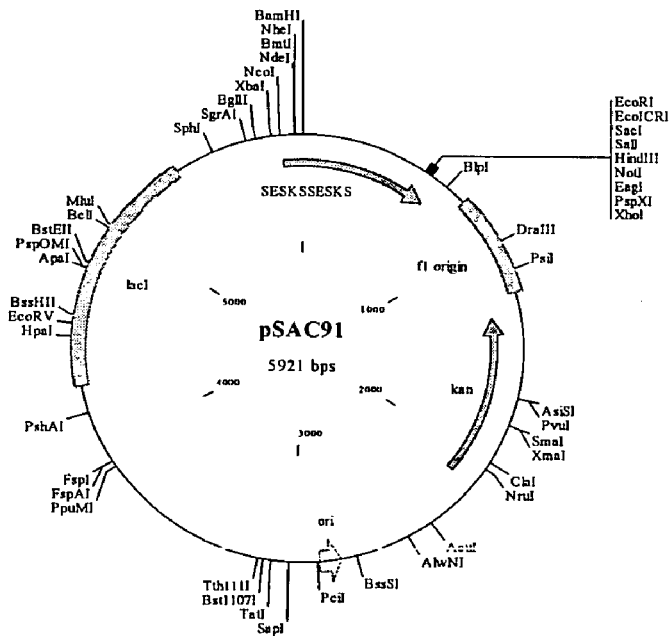
Figure 9 D-E

A.

MSPILGYWKIKGLVQPTRLLLEYLEEKYEEHLYERDEGDKWRNKKFELGLEFPNLPYYID
GDVKLTQSMAIIRYIADKHNMLGGCPKERAEISMLEGAVLDIRYGVSRIAYSKDFETLKV
DFLSKLPEMLKMFEDRLCHKTYLNGDHVTHPDFMLYDALDVVLYMDPMCLDAFPKLV
CFKKRIEAIPQIDKYLKSSKYIAWPLQGWQATFGGGDHPPKSDGSTSGSGHHHHHHSAG
LVPRGSTAIGMKETAAAKFERQHMDSPDLGTGGGSGDDDDKSPMGYRGS<u>TPNHPKPV
LVPKTQNNLQAQNVPQAQNASQAQNAPQAQNAPQAQNAPQVENAPQA</u> *RS* <u>SDSN
LKDLTFEKVKHNLVITNSKKEKVTIQNWFREADFAKEVPNYKATKDEKIEEIIGQN
GERITSKQVDDLIAKGNGKITQDELSKVVDNYELLKHSKNVTNSLDKLISSVSAFTSS
NDSRNVLVAPTSM</u> *RS* EFELRRQALIN

TGTCCCCTATACTAGGTTATTGGAAAATTAAGGGCCTTGTGCAACCCACTCGACTTC
TTTTGGAATATCTTGAAGAAAAATATGAAGAGCATTTGTATGAGCGCGATGAAGGTG
ATAAATGGCGAAACAAAAGTTTGAATTGGGTTTGGAGTTTCCCAATCTTCCTTATT
ATATTGATGGTGATGTTAAATTAACACAGTCTATGGCCATCATACGTTATATAGCTG
ACAAGCACAACATGTTGGGTGGTTGTCCAAAAGAGCGTGCAGAGATTTCAATGCTTG
AAGGAGCGGTTTTGGATATTAGATACGGTGTTTCGAGAATTGCATATAGTAAAGACT
TTGAAACTCTCAAAGTTGATTTTCTTAGCAAGCTACCTGAAATGCTGAAAATGTTCG
AAGATCGTTTATGTCATAAACATATTTAAATGGTGATCATGTAACCCATCCTGACT
TCATGTTGTATGACGCTCTTGATGTTGTTTTATACATGGACCCAATGTGCCTGGATGC
GTTCCCAAAATTAGTTTGTTTTAAAAAACGTATTGAAGCTATCCCACAAATTGATAA
GTACTTGAAATCCAGCAAGTATATAGCATGGCCTTTGCAGGGCTGGCAAGCCACGTT
TGGTGGTGGCGACCATCCTCCAAAATCGGATGGTTCAACTAGTGGTTCTGGTCATCA
CCATCACCATCACTCCGCGGGTCTGGTGCCACGCGGTAGTACTGCAATTGGTATGAA
AGAAACCGCTGCTGCTAAATTCGAACGCCAGCACATGGACAGCCCAGATCTGGGTA
CCGGTGGTGGCTCCGGTGATGACGACGACAAGAGTCCCATGGGATATCGGGGATCC
ACACCGAATCACCCCAAACCAGTACTAGTACCAAAAACACAAAATAATCTTCAAGC
ACAAAATGTTCCTCAGGCACAAAATGCCTCTCAGGCACAAAATGCCCCTCAGGCAC
AAAATGCTCCTCAGGCACAAAATGCTCCTCAGGTGGAAAATGCTCCTCAGGCAAGA
TCCTCTGATTCGAACTTAAAAGATTTAACATTTGAAAAAGTTAAACATAATCTTGTC
ATCACGAATAGCAAAAAAGAGAAAGTGACCATTCAAAACTGGTTCCGAGAGGCTGA
TTTTGCTAAAGAAGTGCCTAATTATAAAGCAACTAAAGATGAGAAAATCGAAGAAA
TCATCGGTCAAAATGGCGAGCGGATCACCTCAAAGCAAGTTGATGATCTTATCGCAA
AAGGTAACGGCAAAATTACCCAAGATGAGCTATCAAAAGTTGTTGATAACTATGAA
TTGCTCAAACATAGCAAAAATGTGACAAACAGCTTAGATAAGTTAATCTCATCTGTA
AGTGCATTTACCTCGTCTAATGATTCGAGAAATGTATTAGTGGCTCCAACTTCAATG
AGATCCGAATTCGAGCTCCGTCGACAAGCTTTAATTAATTA

MSPILGYWKIKGLVQPTRLLLEYLEEKYEEHLYERDEGDKWRNKKFELGLEFPNLPYYID
GDVKLTQSMAIIRYIADKHNMLGGCPKERAEISMLEGAVLDIRYGVSRIAYSKDFETLKV
DFLSKLPEMLKMFEDRLCHKTYLNGDHVTHPDFMLYDALDVVLYMDPMCLDAFPKLV
CFKKRIEAIPQIDKYLKSSKYIAWPLQGWQATFGGGDHPPKSDGSTSGSGHHHHHHSAG
LVPRGSTAIGMKETAAAKFERQHMDSPDLGTGGGSGDDDDKSPMGYRGS<u>TPNHPKPV</u>
<u>LVPKTQNNLQAQNVPQAQNASQAQNAPQAQNAPQAQNAPQVENAPQA</u> *RS* <u>SDSNL</u>
<u>KDLTFEKVKHNLVITNSKKEKVTIQNWFREADFAKEVPNYKATKDEKIEEIIGQNG</u>
<u>ERITSKQVDDLIAKGNGKITQDELSKVVDNYELLKHSKNVTNSLDKLISSVSAFTSSN</u>
<u>DSRNVLVAPTSM</u> *RS* <u>TPNHPKPVLVPKTQNNLQAQNVPQAQNASQAQNAPQAQNA</u>
<u>PQA QNAPQVEN APQA</u> *RS* <u>SDSNLKDLTFEKVKHNLVITNSKKEKVTIQNWFREAD</u>
<u>FAKEVPNYKATKDEKIEEIIGQNGERITSKQVDDLIAKGNGKITQDELSKVVDNYEL</u>
<u>LKHSKNVTNSLDKLISSVSAFTSSNDSRNVLVAPTSM</u> *RS* EFELRRQALIN

TGTCCCCTATACTAGGTTATTGGAAAATTAAGGGCCTTGTGCAACCCACTCGACTTC
TTTTGGAATATCTTGAAGAAAATATGAAGAGCATTTGTATGAGCGCGATGAAGGTG
ATAAATGGCGAAACAAAAAGTTTGAATTGGGTTTGGAGTTTCCCAATCTTCCTTATT
ATATTGATGGTGATGTTAAATTAACACAGTCTATGGCCATCATACGTTATATAGCTG
ACAAGCACAACATGTTGGGTGGTTGTCCAAAAGAGCGTGCAGAGATTTCAATGCTTG
AAGGAGCGGTTTTGGATATTAGATACGGTGTTTCGAGAATTGCATATAGTAAAGACT
TTGAAACTCTCAAAGTTGATTTTCTTAGCAAGCTACCTGAAATGCTGAAAATGTTCG
AAGATCGTTTATGTCATAAAACATATTTAAATGGTGATCATGTAACCCATCCTGACT
TCATGTTGTATGACGCTCTTGATGTTGTTTTATACATGGACCCAATGTGCCTGGATGC
GTTCCCAAAATTAGTTTGTTTTAAAAAACGTATTGAAGCTATCCCACAAATTGATAA
GTACTTGAAATCCAGCAAGTATATAGCATGGCCTTTGCAGGGCTGGCAAGCCACGTT
TGGTGGTGGCGACCATCCTCCAAAATCGGATGGTTCAACTAGTGGTTCTGGTCATCA
CCATCACCATCACTCCGCGGGTCTGGTGCCACGCGGTAGTACTGCAATTGGTATGAA
AGAAACCGCTGCTGCTAAATTCGAACGCCAGCACATGGACAGCCCAGATCTGGGTA
CCGGTGGTGGCTCCGGTGATGACGACGACAAGAGTCCCATGGGATATCGGGGATCC
ACACCGAATCACCCCAAACCAGTACTAGTACCAAAAACACAAAATAATCTTCAAGC
ACAAAATGTTCCTCAGGCACAAAATGCCTCTCAGGCACAAAATGCCCCTCAGGCAC
AAAATGCTCCTCAGGCACAAAATGCTCCTCAGGTGGAAAATGCTCCTCAGGCAAGA
TCCTCTGATTCGAACTTAAAAGATTTAACATTTGAAAAAGTTAAACATAATCTTGTC
ATCACGAATAGCAAAAAGAGAAAGTGACCATTCAAAACTGGTTCCGAGAGGCTGA
TTTTGCTAAAGAAGTGCCTAATTATAAAGCAACTAAAGATGAGAAAATCGAAGAAA
TCATCGGTCAAAATGGCGAGCGGATCACCTCAAAGCAAGTTGATGATCTTATCGCAA
AAGGTAACGGCAAAATTACCCAAGATGAGCTATCAAAAGTTGTTGATAACTATGAA
TTGCTCAAACATAGCAAAAATGTGACAAACAGCTTAGATAAGTTAATCTCATCTGTA
AGTGCATTTACCTCGTCTAATGATTCGAGAAATGTATTAGTGGCTCCAACTTCAATG
AGATCCGAATTCGAGCTCCGTCGACAAGCTTTAATTAATTA

MGSSHHHHHHSSGLVPRGSHMASMTGGQQMGRGSTPNHPKPVLVPKTQNNLQAQ
NVPQAQNASQAQNAPQAQNAPQAQNAPQVENAPQA *RS* SDSNLKDLTFEKVKHNL
VITNSKKEKVTIQNWFREADFAKEVPNYKATKDEKIEEIIGQNGERITSKQVDDLIA
KGNGKITQDELSKVVDNYELLKHSKNVTNSLDKLISSVSAFTSSNDSRNVLVAPTSM
*RS* EFELRRQALIN

B.

ATGGGCAGCAGCCATCATCATCATCATCACAGCAGCGGCCTGGTGCCGCGCGGCAG
CCATATGGCTAGCATGACTGGTGGACAGCAAATGGGTCGCGGATCCACACCGAATC
ACCCCAAACCAGTACTAGTACCAAAAACACAAAATAATCTTCAAGCACAAAATGTT
CCTCAGGCACAAAATGCCTCTCAGGCACAAAATGCCCTCAGGCACAAAATGCTCCT
CAGGCACAAAATGCTCCTCAGGTGGAAAATGCTCCTCAGGCAAGATCCTCTGATTCG
AACTTAAAAGATTTAACATTTGAAAAAGTTAAACATAATCTTGTCATCACGAATAGC
AAAAAAGAGAAAGTGACCATTCAAAACTGGTTCCGAGAGGCTGATTTTGCTAAAGA
AGTGCCTAATTATAAAGCAACTAAAGATGAGAAAATCGAAGAAATCATCGGTCAAA
ATGGCGAGCGGATCACCTCAAAGCAAGTTGATGATCTTATCGCAAAAGGTAACGGC
AAAATTACCCAAGATGAGCTATCAAAAGTTGTTGATAACTATGAATTGCTCAAACAT
AGCAAAAATGTGACAAACAGCTTAGATAAGTTAATCTCATCTGTAAGTGCATTTACC
TCGTCTAATGATTCGAGAAATGTATTAGTGGCTCCAACTTCAATGAGATCCGAATTC
GAGCTCCGTCGACAAGCTTTAATTAATTAA

Figure 12 A-B

A.
MGSSHHHHHHSSGLVPRGSHMASMTGGQQMGRGSTPNHPKPVLVPKTQNNLQAQN
VPQAQNASQAQNAPQAQNAPQAQNAPQVENAPQA RS SDSNLKDLTFEKVKHNLV
ITNSKKEKVTIQNWFREADFAKEVPNYKATKDEKIEEIIGQNGERITSKQVDDLIAK
GNGKITQDELSKVVDNYELLKHSKNVTNSLDKLISSVSAFTSSNDSRNVLVAPTSM
RS TPNHPKPVLVPKTQNNLQAQNVPQAQNASQAQNAPQAQNAPQAQNAPQVENA
PQA RS SDSNLKDLTFEKVKHNLVITNSKKEKVTIQNWFREADFAKEVPNYKATK
DEKIEEIIGQNGERITSKQVDDLIAKGNGKITQDELSKVVDNYELLKHSKNVTNSLD
KL ISSVSAFTSSNDSRNVLVAPTSM RS EFELRRQALIN

ATGGGCAGCAGCCATCATCATCATCATCACAGCAGCGGCCTGGTGCCGCGCGGCAG
CCATATGGCTAGCATGACTGGTGGACAGCAAATGGGTCGCGGATCCACACCGAATC
ACCCCAAACCAGTACTAGTACCAAAAACACAAAATAATCTTCAAGCACAAAATG
TTCCTCAGGCACAAAATGCCTCTCAGGCACAAAATGCCCCTCAGGCACAAAATG
CTCCTCAGGCACAAAATGCTCCTCAGGTGGAAAATGCTCCTCAGGCA AGATCC
TCTGATTCGAACTTAAAAGATTTAACATTTGAAAAGTTAAACATAATCTTGTCA
TCACGAATAGCAAAAAGAGAAAGTGACCATTCAAAACTGGTTCCGAGAGGCT
GATTTTGCTAAAGAAGTGCCTAATTATAAAGCAACTAAAGATGAGAAAATCGAA
GAAATCATCGGTCAAAATGGCGAGCGGATCACCTCAAAGCAAGTTGATGATCTT
ATCGCAAAAGGTAACGGCAAAATTACCCAAGATGAGCTATCAAAAGTTGTTGAT
AACTATGAATTGCTCAAACATAGCAAAAATGTGACAAACAGCTTAGATAAGTTA
ATCTCATCTGTAAGTGCATTTACCTCGTCTAATGATTCGAGAAATGTATTAGTG
GCTCCAACTTCAATG AGATCC ACACCGAATCACCCCAAACCAGTACTAGTACC
AAAAACACAAAATAATCTTCAAGCACAAAATGTTCCTCAGGCACAAAATGCCTC
TCAGGCACAAAATGCCCCTCAGGCACAAAATGCTCCTCAGGCACAAAATGCTCC
TCAGGTGGAAAATGCTCCTCAGGCA AGATCC TCTGATTCGAACTTAAAAGATT
TAACATTTGAAAAGTTAAACATAATCTTGTCATCACGAATAGCAAAAAGAGA
AAGTGACCATTCAAAACTGGTTCCGAGAGGCTGATTTTGCTAAAGAAGTGCCTA
ATTATAAAGCAACTAAAGATGAGAAAATCGAAGAAATCATCGGTCAAAATGGCG
AGCGGATCACCTCAAAGCAAGTTGATGATCTTATCGCAAAAGGTAACGGCAAAA
TTACCCAAGATGAGCTATCAAAAGTTGTTGATAACTATGAATTGCTCAAACATA
GCAAAAATGTGACAAACAGCTTAGATAAGTTAATCTCATCTGTAAGTGCATTTA
CCTCGTCTAATGATTCGAGAAATGTATTAGTGGCTCCAACTTCAATG AGATCC
GAATTCGAGCTCCGTCGACAAGCTTTAATTAATTAA

MGSSHHHHHHSSGLVPRGSHMASMTGGQQMGRGS *GGGGS* QAQNASQQNAPQAQN
APQAQNAPQVENAPQAQNAPQVENAPQ *GGGGS* FREAEFAKTIQNYVATRDDKIE
EIIGQNGERI *GGGGSRSGGGGS* QAQNASQAQNAPQAQNAPQAQNAPQVENAPQAQ
NAPQVENAPQ*GGGGS* FREAEFAKTIQNYVATRDDKIEEIIGQNGERI *GGGGS*
RSEFELRRQACGRTRAPPPPPLRSGC

B.

TGGGCAGCAGCCATCATCATCATCATCACAGCAGCGGCCTGGTGCCGCGCGGCAGC
CATATGGCTAGCATGACTGGTGGACAGCAAATGGGTCGCGGATCCGGTGGCGGCGG
ATCTCAGGCACAAAATGCCTCTCAGGCACAAAATGCCCCTCAGGCACAAAATGCTC
CTCAGGCACAAAATGCTCCTCAGGTGGAAAATGCTCCTCAGGCACAAAATGCTCCTC
AGGTAGAAAATGCTCCTCAAGGTGGCGGTGGCTCGTTCCGTGAAGCAGAGTTTGCA
AAAACAATTCAAAATTATGTTGCAACAAGAGACGATAAAATTGAAGAGATTATCGG
TCAAAATGGTGAACGGATTGGCGGTGGTGGGTCGAGATCCGGTGGCGGCGGATCTC
AGGCACAAAATGCCTCTCAGGCACAAAATGCCCCTCAGGCACAAAATGCTCCTCAG
GCACAAAATGCTCCTCAGGTGGAAAATGCTCCTCAGGCACAAAATGCTCCTCAGGT
AGAAAATGCTCCTCAAGGTGGCGGTGGCTCGTTCCGTGAAGCAGAGTTTGCAAAAA
CAATTCAAAATTATGTTGCAACAAGAGACGATAAAATTGAAGAGATTATCGGTCAA
AATGGTGAACGGATTGGCGGTGGTGGGTCGAGATCCGAATTCGAGCTCCGTCGACA
AGCTTGCGGCCGCACTCGAGCACCACCACCACCACCACTGAGATCCGGCTGCTA

Figure 14A-B

15A
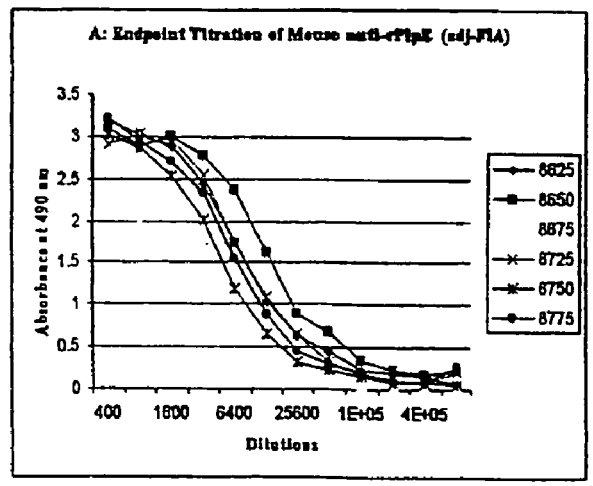
15B
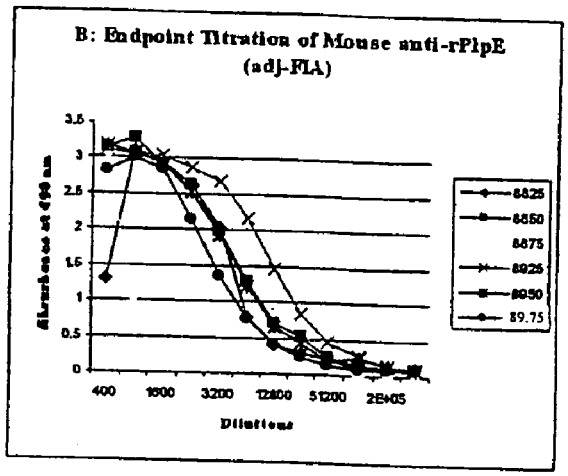
15C
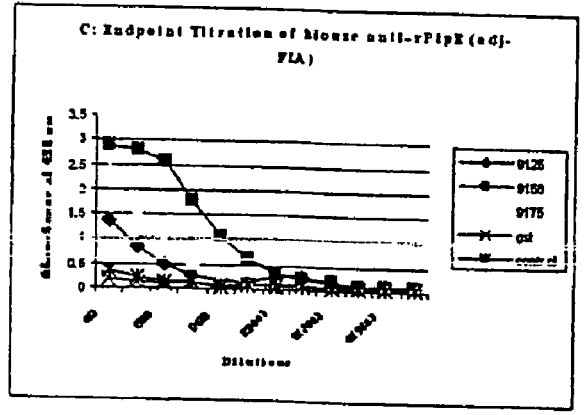
Figure 15 A-C

15D 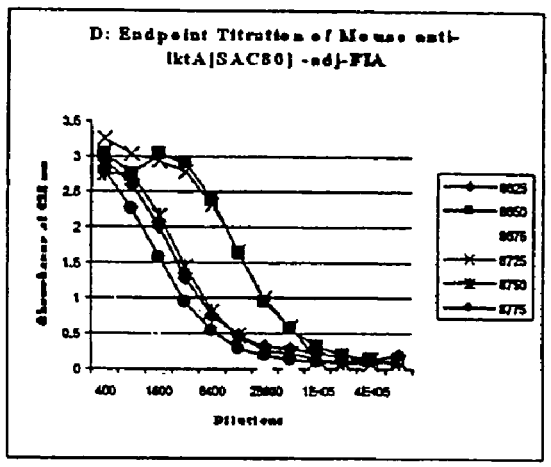
15E 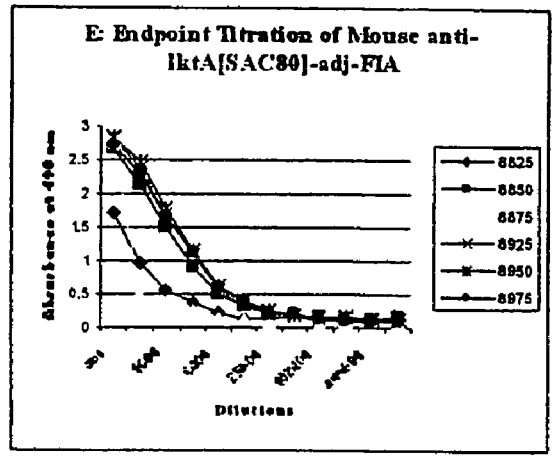
15F 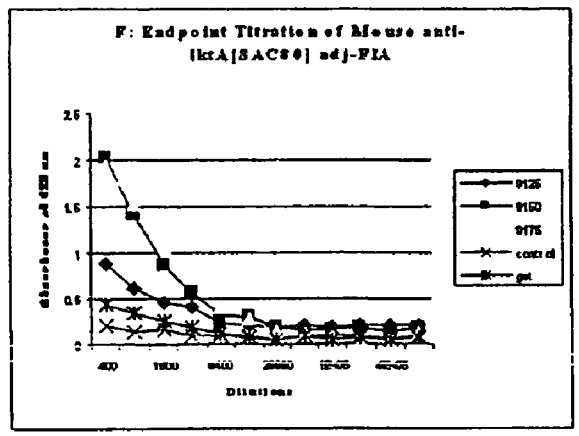
Figure 15 D-F

17A
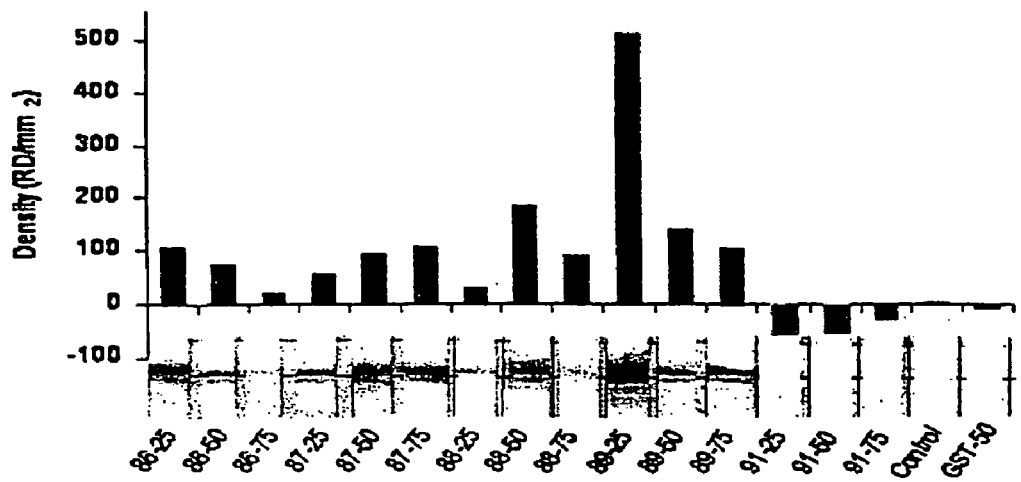
17B
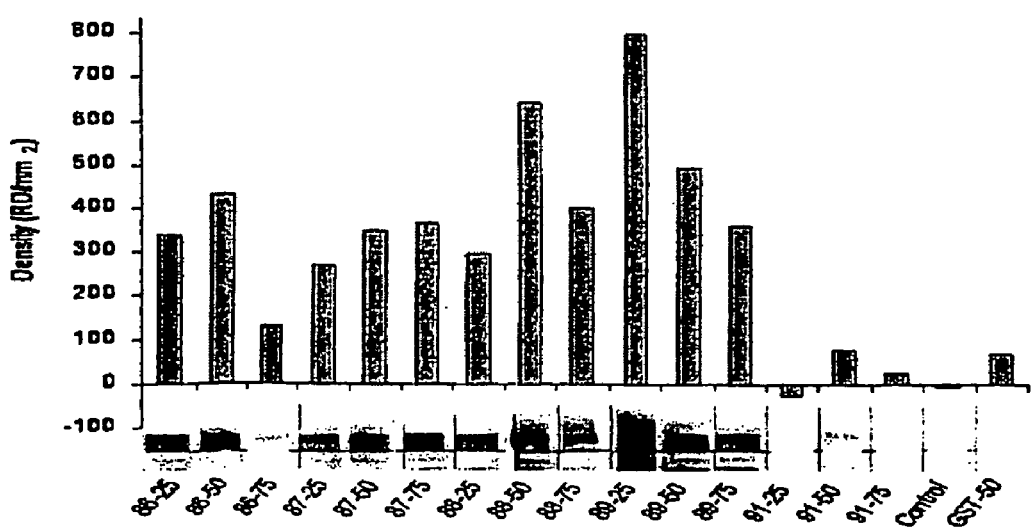
Figure 17 A-B

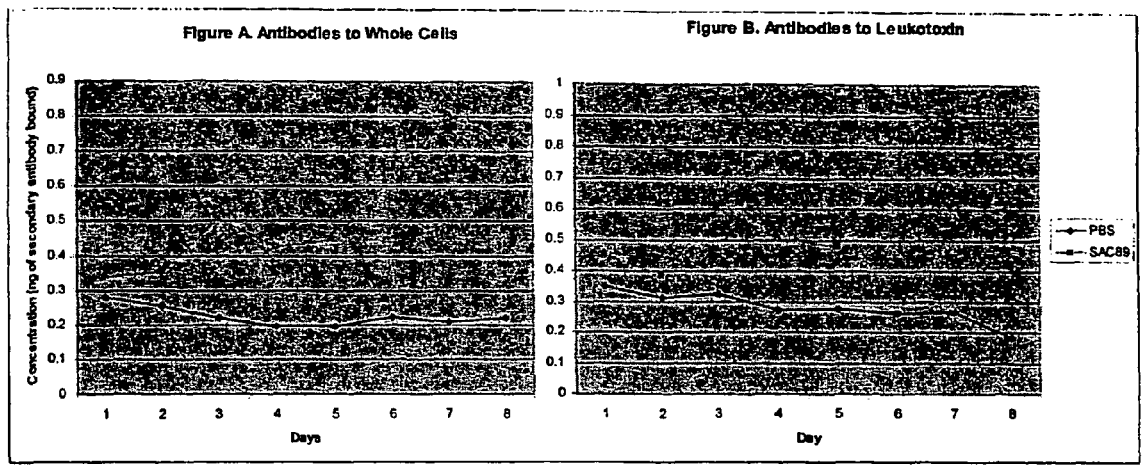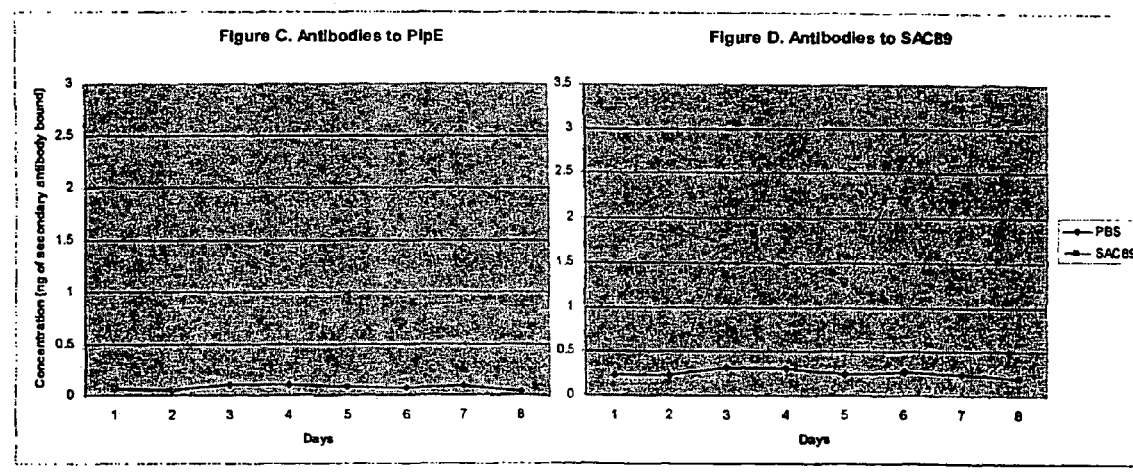
20 A-D

SEQUENCE LISTING

```
<160> NUMBER OF SEQ ID NOS: 35

<210> SEQ ID NO 1
<211> LENGTH: 1310
<212> TYPE: DNA
<213> ORGANISM: Mannheimia haemolytica

<400> SEQUENCE: 1
agggctaatc tactacagcc ccaaaaattt tcataaggga aacgtttacg taaaactcct     60
cagaccactc attcttattt tatataaaaa atgtgataga cttctcgcag tttcgtttta    120
tatatttaag gaataactaa gtgaaattca ataaaaaatt aattttaaca tttgctgcaa    180
ccttagtttt aagtgcttgc ggaggaagcg gtagcggagg ttcgtcttca acaccgaatc    240
accccaaacc agtactagta ccaaaaacac aaaataatct tcaagcacaa aatgttcctc    300
aggcacaaaa tgcctctcag gcacaaaatg cccctcaggc acaaaatgct cctcaggcac    360
aaaatgctcc tcaggtggaa aatgctcctc aggcacaaaa tgctcctcag gtagaaaatg    420
ctcctcaagc agaggttact ccgcctgtac cacagccaca atcacaaaaa attgacggtt    480
cttttgataa aattggttca gtaaaactca ataaagaggc tcaaactctt gagcttagta    540
gattcacttt ggtggataaa ttaggcacac caccgaagtt tgataaagta agcggtaaaa    600
aaattattga agaaaaagat tttctcgtat taaatttgtc tgatattaat gctgaacaac    660
tctctggcga ttttcttatt cgccgtagcg atgatctatt ctatggctac tatcacgata    720
caaatggcaa aaatcttgtc gatgctgccg ataaattcag tcaatatttt gtcgtgtatg    780
atgagaaacg ggtaaatgat aatatctctg ataaattaac agcaacttac cgtaaaaaag    840
aaggctttgt atatggttca aatccacata ctaaagaatt tgccgcacgg atcagcaaat    900
tgggggatgt agaaattaaa tttgaaaatg gtcaagctca aggaagtata aaagacgaaa    960
aagatggaaa tgctgagatc tttactatta aaggtgatac aaaacagtta gagattaccc   1020
caacggaaag taaccgaatc attatagcaa ttttagacca aaatcaaaaa agctatactc   1080
caggaatgga aaaagcaatt atggaaacta agtttattga ttcaaaggct ggtaattccg   1140
```

-continued

```
accaaaaata cttaatcggt gaagcaaaaa gcgataactg gcaagcaata atggttagcg    1200
agaaaaaata aagttatctt ttgctaaaaa ctgaaataaa aaggctgagt ccgggtaata    1260
tcggcctcag tctttaaat tgtagaaaat catctgtaga agatcaaacc                1310
```

<210> SEQ ID NO 2
<211> LENGTH: 337
<212> TYPE: PRT
<213> ORGANISM: Mannheimia haemolytica

<400> SEQUENCE: 2

```
Cys Gly Gly Ser Gly Ser Gly Gly Ser Ser Thr Pro Asn His Pro
 1               5                  10                  15

Lys Pro Val Leu Val Pro Lys Thr Gln Asn Asn Leu Gln Ala Gln Asn
                 20                  25                  30

Val Pro Gln Ala Gln Asn Ala Ser Gln Ala Gln Asn Ala Pro Gln Ala
             35                  40                  45

Gln Asn Ala Pro Gln Ala Gln Asn Ala Pro Gln Val Glu Asn Ala Pro
         50                  55                  60

Gln Ala Gln Asn Ala Pro Gln Val Glu Asn Ala Pro Gln Ala Glu Val
 65                  70                  75                  80

Thr Pro Pro Val Pro Gln Pro Gln Ser Gln Lys Ile Asp Gly Ser Phe
                 85                  90                  95

Asp Lys Ile Gly Ser Val Lys Leu Asn Lys Glu Ala Gln Thr Leu Glu
            100                 105                 110

Leu Ser Arg Phe Thr Leu Val Asp Lys Leu Gly Thr Pro Pro Lys Phe
        115                 120                 125

Asp Lys Val Ser Gly Lys Lys Ile Ile Glu Glu Lys Asp Phe Leu Val
    130                 135                 140

Leu Asn Leu Ser Asp Ile Asn Ala Glu Gln Leu Ser Gly Asp Phe Leu
145                 150                 155                 160

Ile Arg Arg Ser Asp Asp Leu Phe Tyr Gly Tyr Tyr His Asp Thr Asn
                165                 170                 175

Gly Lys Asn Leu Val Asp Ala Ala Asp Lys Phe Ser Gln Tyr Phe Val
            180                 185                 190

Val Tyr Asp Glu Lys Arg Val Asn Asp Asn Ile Ser Asp Lys Leu Thr
        195                 200                 205

Ala Thr Tyr Arg Lys Lys Glu Gly Phe Val Tyr Gly Ser Asn Pro His
    210                 215                 220

Thr Lys Glu Phe Ala Ala Arg Ile Ser Lys Leu Gly Asp Val Glu Ile
225                 230                 235                 240

Lys Phe Glu Asn Gly Gln Ala Gln Gly Ser Ile Lys Asp Glu Lys Asp
                245                 250                 255

Gly Asn Ala Glu Ile Phe Thr Ile Lys Gly Asp Thr Lys Gln Leu Glu
            260                 265                 270

Ile Thr Pro Thr Glu Ser Asn Arg Ile Ile Ile Ala Ile Leu Asp Gln
        275                 280                 285

Asn Gln Lys Ser Tyr Thr Pro Gly Met Glu Lys Ala Ile Met Glu Thr
    290                 295                 300

Lys Phe Ile Asp Ser Lys Ala Gly Asn Ser Asp Gln Lys Tyr Leu Ile
305                 310                 315                 320

Gly Glu Ala Lys Ser Asp Asn Trp Gln Ala Ile Met Val Ser Glu Lys
                325                 330                 335

Lys
```

```
<210> SEQ ID NO 3
<211> LENGTH: 24
<212> TYPE: DNA
<213> ORGANISM: Artificial
<220> FEATURE:
<223> OTHER INFORMATION: oligonucleotide primer

<400> SEQUENCE: 3
cttggatccc aagcacaaaa tgtt                                              24

<210> SEQ ID NO 4
<211> LENGTH: 24
<212> TYPE: DNA
<213> ORGANISM: Artificial
<220> FEATURE:
<223> OTHER INFORMATION: oligonucleotide primer

<400> SEQUENCE: 4
cctggatccc aagcagaggt tact                                              24

<210> SEQ ID NO 5
<211> LENGTH: 24
<212> TYPE: DNA
<213> ORGANISM: Artificial
<220> FEATURE:
<223> OTHER INFORMATION: oligonucleotide primer

<400> SEQUENCE: 5
attggatcca atgctgaaca actc                                              24

<210> SEQ ID NO 6
<211> LENGTH: 33
<212> TYPE: DNA
<213> ORGANISM: Artificial
<220> FEATURE:
<223> OTHER INFORMATION: oligonucleotide primer

<400> SEQUENCE: 6
gactgaattc ttattttttc tcgctaacca tta                                    33

<210> SEQ ID NO 7
<211> LENGTH: 27
<212> TYPE: DNA
<213> ORGANISM: Artificial
<220> FEATURE:
<223> OTHER INFORMATION: oligonucleotide primer

<400> SEQUENCE: 7
gataagcttt taccgtgcgg caaattc                                           27

<210> SEQ ID NO 8
<211> LENGTH: 27
<212> TYPE: DNA
<213> ORGANISM: Artificial
<220> FEATURE:
<223> OTHER INFORMATION: oligonucleotide primer

<400> SEQUENCE: 8
aaaaagcttt tatttaattt ctacatc                                           27

<210> SEQ ID NO 9
<211> LENGTH: 27
<212> TYPE: DNA
<213> ORGANISM: Artificial
<220> FEATURE:
```

<223> OTHER INFORMATION: oligonucleotide primer

<400> SEQUENCE: 9
tttaagcttt tatatacttc cttgagc                                              27

<210> SEQ ID NO 10
<211> LENGTH: 28
<212> TYPE: DNA
<213> ORGANISM: Artificial
<220> FEATURE:
<223> OTHER INFORMATION: oligonucleotide primer

<400> SEQUENCE: 10
gtcaggatcc tgcggaggaa gcggtagc                                             28

<210> SEQ ID NO 11
<211> LENGTH: 16
<212> TYPE: PRT
<213> ORGANISM: Mannheimia haemolytica

<400> SEQUENCE: 11

Pro Asn His Pro Lys Pro Val Leu Val Pro Lys Thr Gln Asn Asn Leu
1               5                   10                  15

<210> SEQ ID NO 12
<211> LENGTH: 43
<212> TYPE: PRT
<213> ORGANISM: Mannheimia haemolytica

<400> SEQUENCE: 12

Gln Asn Ala Ser Gln Ala Gln Asn Ala Pro Gln Ala Gln Asn Ala Pro
1               5                   10                  15

Gln Ala Gln Asn Ala Pro Gln Val Glu Asn Ala Pro Gln Ala Gln Asn
            20                  25                  30

Ala Pro Gln Val Glu Asn Ala Pro Gln Ala Glu
        35                  40

<210> SEQ ID NO 13
<211> LENGTH: 13
<212> TYPE: PRT
<213> ORGANISM: Mannheimia haemolytica

<400> SEQUENCE: 13

Gly Ser Phe Asp Lys Ile Gly Ser Val Lys Leu Asn Lys
1               5                   10

<210> SEQ ID NO 14
<211> LENGTH: 19
<212> TYPE: PRT
<213> ORGANISM: Mannheimia haemolytica

<400> SEQUENCE: 14

Lys Leu Gly Thr Pro Pro Lys Phe Asp Lys Val Ser Gly Lys Lys Ile
1               5                   10                  15

Ile Glu Glu

<210> SEQ ID NO 15
<211> LENGTH: 13
<212> TYPE: PRT
<213> ORGANISM: Mannheimia haemolytica

<400> SEQUENCE: 15

Leu Ile Arg Arg Ser Asp Asp Leu Phe Tyr Gly Tyr Tyr

<210> SEQ ID NO 16
<211> LENGTH: 13
<212> TYPE: PRT
<213> ORGANISM: Mannheimia haemolytica

<400> SEQUENCE: 16

Ala Asp Lys Phe Ser Gln Tyr Phe Val Val Tyr Asp Glu
1               5                   10

<210> SEQ ID NO 17
<211> LENGTH: 13
<212> TYPE: PRT
<213> ORGANISM: Mannheimia haemolytica

<400> SEQUENCE: 17

Asn Ile Ser Asp Lys Leu Thr Ala Thr Tyr Arg Lys Lys
1               5                   10

<210> SEQ ID NO 18
<211> LENGTH: 13
<212> TYPE: PRT
<213> ORGANISM: Mannheimia haemolytica

<400> SEQUENCE: 18

Pro His Thr Lys Glu Phe Ala Ala Arg Ile Ser Lys Leu
1               5                   10

<210> SEQ ID NO 19
<211> LENGTH: 55
<212> TYPE: PRT
<213> ORGANISM: Mannheimia haemolytica

<400> SEQUENCE: 19

Thr Pro Asn His Pro Lys Pro Val Leu Val Pro Lys Thr Gln Asn Asn
1               5                   10                  15

Leu Gln Ala Gln Asn Val Pro Gln Ala Gln Asn Ala Ser Gln Ala Gln
            20                  25                  30

Asn Ala Pro Gln Ala Gln Asn Ala Pro Gln Ala Gln Asn Ala Pro Gln
        35                  40                  45

Val Glu Asn Ala Pro Gln Ala
            50                  55

<210> SEQ ID NO 20
<211> LENGTH: 165
<212> TYPE: DNA
<213> ORGANISM: Mannheimia haemolytica

<400> SEQUENCE: 20
acaccgaatc accccaaacc agtactagta ccaaaaacac aaaataatct tcaagcacaa      60
aatgttcctc aggcacaaaa tgcctctcag gcacaaaatg cccctcaggc acaaaatgct    120
cctcaggcac aaaatgctcc tcaggtggaa aatgctcctc aggca                    165

<210> SEQ ID NO 21
<211> LENGTH: 131
<212> TYPE: PRT
<213> ORGANISM: Mannheimia haemolytica

<400> SEQUENCE: 21

Ser Asp Ser Asn Leu Lys Asp Leu Thr Phe Glu Lys Val Lys His Asn
1               5                   10                  15

-continued

Leu Val Ile Thr Asn Ser Lys Lys Glu Lys Val Thr Ile Gln Asn Trp
            20                  25                  30

Phe Arg Glu Ala Asp Phe Ala Lys Glu Val Pro Asn Tyr Lys Ala Thr
            35                  40                  45

Lys Asp Glu Lys Ile Glu Glu Ile Ile Gly Gln Asn Gly Glu Arg Ile
        50                  55                  60

Thr Ser Lys Gln Val Asp Asp Leu Ile Ala Lys Gly Asn Gly Lys Ile
65                  70                  75                  80

Thr Gln Asp Glu Leu Ser Lys Val Val Asp Asn Tyr Glu Leu Leu Lys
                85                  90                  95

His Ser Lys Asn Val Thr Asn Ser Leu Asp Lys Leu Ile Ser Ser Val
            100                 105                 110

Ser Ala Phe Thr Ser Ser Asn Asp Ser Arg Asn Val Leu Val Ala Pro
        115                 120                 125

Thr Ser Met
    130

<210> SEQ ID NO 22
<211> LENGTH: 393
<212> TYPE: DNA
<213> ORGANISM: Mannheimia haemolytica

<400> SEQUENCE: 22
tctgattcga acttaaaaga tttaacattt gaaaaagtta acataatcct tgtcatcacg    60
aatagcaaaa aagagaaagt gaccattcaa aactggttcc gagaggctga ttttgctaaa   120
gaagtgccta attataaagc aactaaagat gagaaaatcg aagaaatcat cggtcaaaat   180
ggcgagcgga tcacctcaaa gcaagttgat gatcttatcg caaaaggtaa cggcaaaatt   240
acccaagatg agctatcaaa agttgttgat aactatgaat tgctcaaaca tagcaaaaat   300
gtgacaaaca gcttagataa gttaatctca tctgtaagtg catttacctc gtctaatgat   360
tcgagaaatg tattagtggc tccaacttca atg                                393

<210> SEQ ID NO 23
<211> LENGTH: 486
<212> TYPE: PRT
<213> ORGANISM: Mannheimia haemolytica

<400> SEQUENCE: 23

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

```
Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Lys Ser Pro Met Gly Tyr Arg Gly Ser Thr Pro Asn
        275                 280                 285

His Pro Lys Pro Val Leu Val Pro Lys Thr Gln Asn Asn Leu Gln Ala
    290                 295                 300

Gln Asn Val Pro Gln Ala Gln Asn Ala Ser Gln Ala Gln Asn Ala Pro
305                 310                 315                 320

Gln Ala Gln Asn Ala Pro Gln Ala Gln Asn Ala Pro Gln Val Glu Asn
                325                 330                 335

Ala Pro Gln Ala Arg Ser Ser Asp Ser Asn Leu Lys Asp Leu Thr Phe
            340                 345                 350

Glu Lys Val Lys His Asn Leu Val Ile Thr Asn Ser Lys Lys Glu Lys
        355                 360                 365

Val Thr Ile Gln Asn Trp Phe Arg Glu Ala Asp Phe Ala Lys Glu Val
    370                 375                 380

Pro Asn Tyr Lys Ala Thr Lys Asp Glu Lys Ile Glu Glu Ile Ile Gly
385                 390                 395                 400

Gln Asn Gly Glu Arg Ile Thr Ser Lys Gln Val Asp Asp Leu Ile Ala
                405                 410                 415

Lys Gly Asn Gly Lys Ile Thr Gln Asp Glu Leu Ser Lys Val Val Asp
            420                 425                 430

Asn Tyr Glu Leu Leu Lys His Ser Lys Asn Val Thr Asn Ser Leu Asp
        435                 440                 445

Lys Leu Ile Ser Ser Val Ser Ala Phe Thr Ser Ser Asn Asp Ser Arg
    450                 455                 460

Asn Val Leu Val Ala Pro Thr Ser Met Arg Ser Glu Phe Glu Leu Arg
465                 470                 475                 480

Arg Gln Ala Leu Ile Asn
                485

<210> SEQ ID NO 24
<211> LENGTH: 1459
<212> TYPE: DNA
<213> ORGANISM: Mannheimia haemolytica

<400> SEQUENCE: 24
tgtcccctat actaggttat tggaaaatta agggccttgt gcaacccact cgacttcttt     60
```

-continued

```
tggaatatct tgaagaaaaa tatgaagagc atttgtatga gcgcgatgaa ggtgataaat      120
ggcgaaacaa aaagtttgaa ttgggtttgg agtttcccaa tcttccttat tatattgatg      180
gtgatgttaa attaacacag tctatggcca tcatacgtta tatagctgac aagcacaaca      240
tgttgggtgg ttgtccaaaa gagcgtgcag agatttcaat gcttgaagga gcggttttgg      300
atattagata cggtgtttcg agaattgcat atagtaaaga ctttgaaact ctcaaagttg      360
attttcttag caagctacct gaaatgctga aaatgttcga agatcgttta tgtcataaaa      420
catatttaaa tggtgatcat gtaacccatc ctgacttcat gttgtatgac gctcttgatg      480
ttgttttata catggaccca atgtgcctgg atgcgttccc aaaattagtt tgttttaaaa      540
aacgtattga agctatccca caaattgata agtacttgaa atccagcaag tatatagcat      600
ggcctttgca gggctggcaa gccacgtttg gtggtggcga ccatcctcca aaatcggatg      660
gttcaactag tggttctggt catcaccatc accatcactc cgcgggtctg gtgccacgcg      720
gtagtactgc aattggtatg aaagaaaccg ctgctgctaa attcgaacgc agcacatgg      780
acagcccaga tctgggtacc ggtggtggct ccggtgatga cgacgacaag agtcccatgg      840
gatatcgggg atccacaccg aatcacccca aaccagtact agtaccaaaa acacaaaata      900
atcttcaagc acaaaatgtt cctcaggcac aaaatgcctc tcaggcacaa aatgcccctc      960
aggcacaaaa tgctcctcag gcacaaaatg ctccctcaggt ggaaaatgct cctcaggcaa     1020
gatcctctga ttcgaactta aaagatttaa catttgaaaa agttaaacat aatcttgtca     1080
tcacgaatag caaaaaagag aaagtgacca ttcaaaactg gttccgagag gctgattttg     1140
ctaaagaagt gcctaattat aaagcaacta agatgagaaa atcgaagaa atcatcggtc      1200
aaaatggcga gcggatcacc tcaaagcaag ttgatgatct tatcgcaaaa ggtaacggca     1260
aaattaccca agatgagcta tcaaaagttg ttgataacta tgaattgctc aaacatagca     1320
aaaatgtgac aaacagctta gataagttaa tctcatctgt aagtgcattt acctcgtcta     1380
atgattcgag aaatgtatta gtggctccaa cttcaatgag atccgaattc gagctccgtc     1440
gacaagcttt aattaatta                                                  1459
```

<210> SEQ ID NO 25
<211> LENGTH: 676
<212> TYPE: PRT
<213> ORGANISM: Mannaheimia haemolytica

<400> SEQUENCE: 25

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125
```

-continued

```
Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Gly Ser Thr Ser
210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Ser Pro Met Gly Tyr Arg Gly Ser Thr Pro Asn
            275                 280                 285

His Pro Lys Pro Val Leu Val Pro Lys Thr Gln Asn Asn Leu Gln Ala
            290                 295                 300

Gln Asn Val Pro Gln Ala Gln Asn Ala Ser Gln Ala Gln Asn Ala Pro
305                 310                 315                 320

Gln Ala Gln Asn Ala Pro Gln Ala Gln Asn Ala Pro Gln Val Glu Asn
                325                 330                 335

Ala Pro Gln Ala Arg Ser Ser Asp Ser Asn Leu Lys Asp Leu Thr Phe
            340                 345                 350

Glu Lys Val Lys His Asn Leu Val Ile Thr Asn Ser Lys Lys Glu Lys
            355                 360                 365

Val Thr Ile Gln Asn Trp Phe Arg Glu Ala Asp Phe Ala Lys Glu Val
370                 375                 380

Pro Asn Tyr Lys Ala Thr Lys Asp Glu Lys Ile Glu Glu Ile Ile Gly
385                 390                 395                 400

Gln Asn Gly Glu Arg Ile Thr Ser Lys Gln Val Asp Asp Leu Ile Ala
                405                 410                 415

Lys Gly Asn Gly Lys Ile Thr Gln Asp Glu Leu Ser Lys Val Val Asp
            420                 425                 430

Asn Tyr Glu Leu Leu Lys His Ser Lys Asn Val Thr Asn Ser Leu Asp
            435                 440                 445

Lys Leu Ile Ser Ser Val Ser Ala Phe Thr Ser Ser Asn Asp Ser Arg
            450                 455                 460

Asn Val Leu Val Ala Pro Thr Ser Met Arg Ser Thr Pro Asn His Pro
465                 470                 475                 480

Lys Pro Val Leu Val Pro Lys Thr Gln Asn Asn Leu Gln Ala Gln Asn
                485                 490                 495

Val Pro Gln Ala Gln Asn Ala Ser Gln Ala Gln Asn Ala Pro Gln Ala
            500                 505                 510

Gln Asn Ala Pro Gln Ala Gln Asn Ala Pro Gln Val Glu Asn Ala Pro
            515                 520                 525

Gln Ala Arg Ser Ser Asp Ser Asn Leu Lys Asp Leu Thr Phe Glu Lys
530                 535                 540
```

```
Val Lys His Asn Leu Val Ile Thr Asn Ser Lys Lys Glu Lys Val Thr
545                 550                 555                 560

Ile Gln Asn Trp Phe Arg Glu Ala Asp Phe Ala Lys Glu Val Pro Asn
                565                 570                 575

Tyr Lys Ala Thr Lys Asp Glu Lys Ile Glu Glu Ile Ile Gly Gln Asn
            580                 585                 590

Gly Glu Arg Ile Thr Ser Lys Gln Val Asp Asp Leu Ile Ala Lys Gly
        595                 600                 605

Asn Gly Lys Ile Thr Gln Asp Glu Leu Ser Lys Val Val Asp Asn Tyr
    610                 615                 620

Glu Leu Leu Lys His Ser Lys Asn Val Thr Asn Ser Leu Asp Lys Leu
625                 630                 635                 640

Ile Ser Ser Val Ser Ala Phe Thr Ser Ser Asn Asp Ser Arg Asn Val
                645                 650                 655

Leu Val Ala Pro Thr Ser Met Arg Ser Glu Phe Glu Leu Arg Arg Gln
            660                 665                 670

Ala Leu Ile Asn
        675

<210> SEQ ID NO 26
<211> LENGTH: 1459
<212> TYPE: DNA
<213> ORGANISM: Mannheimia haemolytica

<400> SEQUENCE: 26
tgtcccctat actaggttat tggaaaatta agggccttgt gcaacccact cgacttcttt      60
tggaatatct tgaagaaaaa tatgaagagc atttgtatga gcgcgatgaa ggtgataaat     120
ggcgaaacaa aaagtttgaa ttgggtttgg agtttcccaa tcttccttat tatattgatg     180
gtgatgttaa attaacacag tctatggcca tcatacgtta tatagctgac aagcacaaca     240
tgttgggtgg ttgtccaaaa gagcgtgcag agatttcaat gcttgaagga gcggttttgg     300
atattagata cggtgtttcg agaattgcat atagtaaaga ctttgaaact ctcaaagttg     360
attttcttag caagctacct gaaatgctga aaatgttcga agatcgttta tgtcataaaa     420
catatttaaa tggtgatcat gtaacccatc ctgacttcat gttgtatgac gctcttgatg     480
ttgtttata catggaccca atgtgcctgg atgcgttccc aaaattagtt tgttttaaaa     540
aacgtattga agctatccca caaattgata agtacttgaa atccagcaag tatatagcat     600
ggcctttgca gggctggcaa gccacgtttg tggtggcga ccatcctcca aaatcggatg     660
gttcaactag tggttctggt catcaccatc accatcactc cgcgggtctg gtgccacgcg     720
gtagtactgc aattggtatg aaagaaaccg ctgctgctaa attcgaacgc agcacatgg     780
acagcccaga tctgggtacc ggtggtggct ccggtgatga cgacgacaag agtcccatgg     840
gatatcgggg atcacaccg aatcacccca accagtact agtaccaaaa acacaaaata     900
atcttcaagc acaaaatgtt cctcaggcac aaaatgcctc tcaggcacaa atgcccctc     960
aggcacaaaa tgctcctcag gcacaaaatg ctcctcaggt ggaaaatgct cctcaggcaa    1020
gatcctctga ttcgaactta aaagatttaa catttgaaaa agttaaacat aatcttgtca    1080
tcacgaatag caaaaagag aaagtgacca ttcaaaactg gttccgagag gctgattttg    1140
ctaaagaagt gcctaattat aaagcaacta agatgagaa aatcgaagaa atcatcggtc    1200
aaaatggcga gcggatcacc tcaaagcaag ttgatgatct tatcgcaaaa ggtaacggca    1260
aaattaccca agatgagcta tcaaaagttg ttgataacta tgaattgctc aaacatagca    1320
```

```
aaaatgtgac aaacagctta gataagttaa tctcatctgt aagtgcattt acctcgtcta   1380
atgattcgag aaatgtatta gtggctccaa cttcaatgag atccgaattc gagctccgtc   1440
gacaagcttt aattaatta                                                1459
```

<210> SEQ ID NO 27
<211> LENGTH: 235
<212> TYPE: PRT
<213> ORGANISM: Mannheimia haemolytica

<400> SEQUENCE: 27

```
Met Gly Ser Ser His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Thr Pro Asn His Pro Lys Pro Val Leu Val Pro Lys Thr Gln
            35                  40                  45

Asn Asn Leu Gln Ala Gln Asn Val Pro Gln Ala Gln Asn Ala Ser Gln
50                  55                  60

Ala Gln Asn Ala Pro Gln Ala Gln Asn Ala Pro Gln Ala Gln Asn Ala
65                  70                  75                  80

Pro Gln Val Glu Asn Ala Pro Gln Ala Arg Ser Ser Asp Ser Asn Leu
                85                  90                  95

Lys Asp Leu Thr Phe Glu Lys Val Lys His Asn Leu Val Ile Thr Asn
            100                 105                 110

Ser Lys Lys Glu Lys Val Thr Ile Gln Asn Trp Phe Arg Glu Ala Asp
            115                 120                 125

Phe Ala Lys Glu Val Pro Asn Tyr Lys Ala Thr Lys Asp Glu Lys Ile
130                 135                 140

Glu Glu Ile Ile Gly Gln Asn Gly Glu Arg Ile Thr Ser Lys Gln Val
145                 150                 155                 160

Asp Asp Leu Ile Ala Lys Gly Asn Gly Lys Ile Thr Gln Asp Glu Leu
                165                 170                 175

Ser Lys Val Val Asp Asn Tyr Glu Leu Leu Lys His Ser Lys Asn Val
            180                 185                 190

Thr Asn Ser Leu Asp Lys Leu Ile Ser Ser Val Ser Ala Phe Thr Ser
            195                 200                 205

Ser Asn Asp Ser Arg Asn Val Leu Val Ala Pro Thr Ser Met Arg Ser
210                 215                 220

Glu Phe Glu Leu Arg Arg Gln Ala Leu Ile Asn
225                 230                 235
```

<210> SEQ ID NO 28
<211> LENGTH: 1278
<212> TYPE: DNA
<213> ORGANISM: Mannheimia haemolytica

<400> SEQUENCE: 28

```
atgggcagca gccatcatca tcatcatcac agcagcggcc tggtgccgcg cggcagccat   60
atggctagca tgactggtgg acagcaaatg ggtcgcggat ccacaccgaa tcaccccaaa   120
ccagtactag taccaaaaac acaaataat cttcaagcac aaaatgttcc tcaggcacaa   180
aatgcctctc aggcacaaaa tgcccctcag gcacaaaatg ctcctcaggc acaaaatgct   240
cctcaggtgg aaaatgctcc tcaggcaaga tcctctgatt cgaacttaaa agatttaaca   300
tttgaaaaag ttaaacataa tcttgtcatc acgaatagca aaaagagaa agtgaccatt   360
```

-continued

```
caaaactggt tccgagaggc tgattttgct aaagaagtgc ctaattataa agcaactaaa      420
gatgagaaaa tcgaagaaat catcggtcaa aatggcgagc ggatcaccto aaagcaagtt      480 gatgatctta tcgcaaaagg taacggcaaa attacccaag atgagctatc aaaagttgtt      540
gataactatg aattgctcaa acatagcaaa aatgtgacaa acagcttaga taagttaatc      600
tcatctgtaa gtgcatttac ctcgtctaat gattcgagaa atgtattagt ggctccaact      660
tcaatgagat ccacaccgaa tcaccccaaa ccagtactag taccaaaaac acaaataat       720 cttcaagcac aaaatgttcc tcaggcacaa aatgcctctc aggcacaaaa tgcccctcag      780
gcacaaaatg ctcctcaggc acaaaatgct cctcaggtgg aaaatgctcc tcaggcaaga      840
tcctctgatt cgaacttaaa agatttaaca tttgaaaaag ttaaacataa tcttgtcatc      900
acgaatagca aaaagagaa agtgaccatt caaaactggt tccgagaggc tgattttgct       960
aaagaagtgc ctaattataa agcaactaaa gatgagaaaa tcgaagaaat catcggtcaa     1020
aatggcgagc ggatcaccto aaagcaagtt gatgatctta tcgcaaaagg taacggcaaa     1080
attacccaag atgagctatc aaaagttgtt gataactatg aattgctcaa acatagcaaa     1140
aatgtgacaa acagcttaga taagttaatc tcatctgtaa gtgcatttac ctcgtctaat     1200
gattcgagaa atgtattagt ggctccaact tcaatgagat ccgaattcga gctccgtcga     1260
caagctttaa ttaattaa                                                    1278
```

<210> SEQ ID NO 29
<211> LENGTH: 425
<212> TYPE: PRT
<213> ORGANISM: Mannheimia haemolytica

<400> SEQUENCE: 29

```
Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Thr Pro Asn His Pro Lys Pro Val Leu Val Pro Lys Thr Gln
        35                  40                  45

Asn Asn Leu Gln Ala Gln Asn Val Pro Gln Ala Gln Asn Ala Ser Gln
    50                  55                  60

Ala Gln Asn Ala Pro Gln Ala Gln Asn Ala Pro Gln Ala Gln Asn Ala
65                  70                  75                  80

Pro Gln Val Glu Asn Ala Pro Gln Ala Arg Ser Ser Asp Ser Asn Leu
                85                  90                  95

Lys Asp Leu Thr Phe Glu Lys Val Lys His Asn Leu Val Ile Thr Asn
            100                 105                 110

Ser Lys Lys Glu Lys Val Thr Ile Gln Asn Trp Phe Arg Glu Ala Asp
        115                 120                 125

Phe Ala Lys Glu Val Pro Asn Tyr Lys Ala Thr Lys Asp Glu Lys Ile
    130                 135                 140

Glu Glu Ile Ile Gly Gln Asn Gly Glu Arg Ile Thr Ser Lys Gln Val
145                 150                 155                 160

Asp Asp Leu Ile Ala Lys Gly Asn Gly Lys Ile Thr Gln Asp Glu Leu
                165                 170                 175

Ser Lys Val Val Asp Asn Tyr Glu Leu Leu Lys His Ser Lys Asn Val
            180                 185                 190

Thr Asn Ser Leu Asp Lys Leu Ile Ser Ser Val Ser Ala Phe Thr Ser
        195                 200                 205
```

-continued

```
Ser Asn Asp Ser Arg Asn Val Leu Val Ala Pro Thr Ser Met Arg Ser
    210                 215                 220
Thr Pro Asn His Pro Lys Pro Val Leu Val Pro Lys Thr Gln Asn Asn
225                 230                 235                 240
Leu Gln Ala Gln Asn Val Pro Gln Ala Gln Asn Ala Ser Gln Ala Gln
                245                 250                 255
Asn Ala Pro Gln Ala Gln Asn Ala Pro Gln Ala Gln Asn Ala Pro Gln
                260                 265                 270
Val Glu Asn Ala Pro Gln Ala Arg Ser Ser Asp Ser Asn Leu Lys Asp
            275                 280                 285
Leu Thr Phe Glu Lys Val Lys His Asn Leu Val Ile Thr Asn Ser Lys
    290                 295                 300
Lys Glu Lys Val Thr Ile Gln Asn Trp Phe Arg Glu Ala Asp Phe Ala
305                 310                 315                 320
Lys Glu Val Pro Asn Tyr Lys Ala Thr Lys Asp Glu Lys Ile Glu Glu
                325                 330                 335
Ile Ile Gly Gln Asn Gly Glu Arg Ile Thr Ser Lys Gln Val Asp Asp
                340                 345                 350
Leu Ile Ala Lys Gly Asn Gly Lys Ile Thr Gln Asp Glu Leu Ser Lys
            355                 360                 365
Val Val Asp Asn Tyr Glu Leu Leu Lys His Ser Lys Asn Val Thr Asn
    370                 375                 380
Ser Leu Asp Lys Leu Ile Ser Ser Val Ser Ala Phe Thr Ser Ser Asn
385                 390                 395                 400
Asp Ser Arg Asn Val Leu Val Ala Pro Thr Ser Met Arg Ser Glu Phe
                405                 410                 415
Glu Leu Arg Arg Gln Ala Leu Ile Asn
            420                 425

<210> SEQ ID NO 30
<211> LENGTH: 1278
<212> TYPE: DNA
<213> ORGANISM: Mannheimia haemolytica

<400> SEQUENCE: 30
atgggcagca gccatcatca tcatcatcac agcagcggcc tggtgccgcg cggcagccat      60
atggctagca tgactggtgg acagcaaatg ggtcgcggat ccacaccgaa tcaccccaaa     120
ccagtactag taccaaaaac acaaataat cttcaagcac aaaatgttcc tcaggcacaa     180
aatgcctctc aggcacaaaa tgcccctcag gcacaaaatg ctcctcaggc acaaaatgct     240
cctcaggtgg aaaatgctcc tcaggcaaga tcctctgatt cgaacttaaa agatttaaca     300
tttgaaaaag ttaaacataa tcttgtcatc acgaatagca aaaagagaa agtgaccatt     360 caaaactggt tccgagaggc tgattttgct aagaagtgc ctaattataa agcaactaaa     420
gatgagaaaa tcgaagaaat catcggtcaa atggcgagc ggatcacctc aaagcaagtt     480
gatgatctta cgcaaaagg taacggcaaa attacccaag atgagctatc aaaagttgtt     540
gataactatg aattgctcaa acatagcaaa atgtgacaa acagcttaga taagttaatc     600
tcatctgtaa gtgcatttac ctcgtctaat gattcgagaa atgtattagt ggctccaact     660
tcaatgagat ccacaccgaa tcaccccaaa ccagtactag taccaaaaac acaaataat     720 cttcaagcac aaaatgttcc tcaggcacaa aatgcctctc aggcacaaaa tgcccctcag     780
gcacaaaatg ctcctcaggc acaaaatgct cctcaggtgg aaaatgctcc tcaggcaaga     840
tcctctgatt cgaacttaaa agatttaaca tttgaaaaag ttaaacataa tcttgtcatc     900
```

```
acgaatagca aaaagagaa agtgaccatt caaaactggt tccgagaggc tgattttgct      960
aaagaagtgc ctaattataa agcaactaaa gatgagaaaa tcgaagaaat catcggtcaa     1020
aatggcgagc ggatcacctc aaagcaagtt gatgatctta tcgcaaaagg taacggcaaa     1080
attacccaag atgagctatc aaaagttgtt gataactatg aattgctcaa acatagcaaa     1140
aatgtgacaa acagcttaga taagttaatc tcatctgtaa gtgcatttac ctcgtctaat     1200
gattcgagaa atgtattagt ggctccaact tcaatgagat ccgaattcga gctccgtcga     1260
caagctttaa ttaattaa                                                   1278
```

<210> SEQ ID NO 31
<211> LENGTH: 242
<212> TYPE: PRT
<213> ORGANISM: Mannheimia haemolytica

<400> SEQUENCE: 31

```
Met Gly Ser Ser His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Gly Gly Gly Ser Gln Ala Gln Asn Ala Ser Gln Ala Gln
        35                  40                  45

Asn Ala Pro Gln Ala Gln Asn Ala Pro Gln Ala Asn Ala Pro Gln
    50                  55                  60

Val Glu Asn Ala Pro Gln Ala Gln Asn Ala Pro Gln Val Glu Asn Ala
65                  70                  75                  80

Pro Gln Gly Gly Gly Gly Ser Phe Arg Glu Ala Glu Phe Ala Lys Thr
                85                  90                  95

Ile Gln Asn Tyr Val Ala Thr Arg Asp Asp Lys Ile Glu Glu Ile Ile
            100                 105                 110

Gly Gln Asn Gly Glu Arg Ile Gly Gly Gly Ser Arg Ser Gly Gly
        115                 120                 125

Gly Gly Ser Gln Ala Gln Asn Ala Ser Gln Ala Gln Asn Ala Pro Gln
130                 135                 140

Ala Gln Asn Ala Pro Gln Ala Gln Asn Ala Pro Gln Val Glu Asn Ala
145                 150                 155                 160

Pro Gln Ala Gln Asn Ala Pro Gln Val Glu Asn Ala Pro Gln Gly Gly
                165                 170                 175

Gly Gly Ser Phe Arg Glu Ala Glu Phe Ala Lys Thr Ile Gln Asn Tyr
            180                 185                 190

Val Ala Thr Arg Asp Asp Lys Ile Glu Glu Ile Ile Gly Gln Asn Gly
        195                 200                 205

Glu Arg Ile Gly Gly Gly Ser Arg Ser Glu Phe Glu Leu Arg Arg
    210                 215                 220

Gln Ala Cys Gly Arg Thr Arg Ala Pro Pro Pro Pro Leu Arg Ser
225                 230                 235                 240

Gly Cys
```

<210> SEQ ID NO 32
<211> LENGTH: 727
<212> TYPE: DNA
<213> ORGANISM: Mannheimia haemolytica

<400> SEQUENCE: 32

```
tgggcagcag ccatcatcat catcatcaca gcagcggcct ggtgccgcgc ggcagccata      60
```

```
tggctagcat gactggtgga cagcaaatgg gtcgcggatc cggtggcggc ggatctcagg      120
cacaaaatgc ctctcaggca caaaatgccc ctcaggcaca aaatgctcct caggcacaaa      180
atgctcctca ggtggaaaat gctcctcagg cacaaaatgc tcctcaggta gaaaatgctc      240
ctcaaggtgg cggtggctcg ttccgtgaag cagagtttgc aaaaacaatt caaaattatg      300
ttgcaacaag agacgataaa attgaagaga ttatcggtca aaatggtgaa cggattggcg      360
gtggtgggtc gagatccggt ggcggcggat ctcaggcaca aaatgcctct caggcacaaa      420
atgcccctca ggcacaaaat gctcctcagg cacaaaatgc tcctcaggtg gaaaatgctc      480
ctcaggcaca aaatgctcct caggtagaaa atgctcctca aggtggcggt ggctcgttcc      540
gtgaagcaga gtttgcaaaa acaattcaaa attatgttgc aacaagagac gataaaattg      600
aagagattat cggtcaaaat ggtgaacgga ttggcggtgg tgggtcgaga tccgaattcg      660
agctccgtcg acaagcttgc ggccgcactc gagcaccacc accaccacca ctgagatccg      720
gctgcta                                                               727
```

<210> SEQ ID NO 33
<211> LENGTH: 5
<212> TYPE: PRT
<213> ORGANISM: Mannheimia haemolytica

<400> SEQUENCE: 33

Gln Asn Ala Pro Gln
1               5

<210> SEQ ID NO 34
<211> LENGTH: 4
<212> TYPE: PRT
<213> ORGANISM: Artificial
<220> FEATURE:
<223> OTHER INFORMATION: spacer peptide

<400> SEQUENCE: 34

Gly Gly Gly Ser
1

<210> SEQ ID NO 35
<211> LENGTH: 5
<212> TYPE: PRT
<213> ORGANISM: Artificial
<220> FEATURE:
<223> OTHER INFORMATION: Synthetic linker/spacer sequence

<400> SEQUENCE: 35

Gly Gly Gly Gly Ser
1               5

MANNHEIMIA HAEMOLYTICA CHIMERIC OUTER MEMBRANE PROTEIN PLPE AND LEUKOTOXIN EPITOPES AS A VACCINE OR VACCINE COMPONENT AGAINST SHIPPING FEVER

CROSS-REFERENCE TO RELATED APPLICATIONS

This application claims benefit of U.S. provisional patent application 60/757,342, filed Jan. 9, 2006, and is a continuation-in-part of U.S. patent application Ser. No. 11/235,982, filed Sep. 27, 2005, now issued U.S. Pat. No. 7,144,580, which is a divisional of U.S. patent application Ser. No. 10/695,544, filed Oct 29, 2003, now abandoned, which claimed benefit of U.S. provisional patent application 60/422,305, filed Oct 30, 2002, the complete contents of each of which are hereby incorporated by reference.

This invention was made using funds from grants from the United States Department of Agriculture having grant number USDA-NRI 2002-35204-12250. The United States government may have certain rights in this invention.

BACKGROUND OF THE INVENTION

1. Field of the Invention

The present invention relates generally to the prevention of bovine respiratory disease (BRD) and, in particular, its most severe form, termed "shipping fever". More specifically, the present invention relates to the use of chimeric proteins comprising immunodominant epitopes of recombinant *Mannheimia haemolytica* outer membrane protein PlpE, and immunodominant epitopes of recombinant *M. haemolytica* leukotoxin as a vaccine or vaccine component against shipping fever.

2. Background

BRD is the major cause of beef cattle morbidity and mortality and of economic losses to the beef cattle industry. The cost of BRD to beef cattle producers approaches $1 billion annually. BRD arises from the interaction of numerous contributing factors including physical stresses associated with weaning, shipment, inclement weather, and overcrowding coupled with viral and bacterial infections. The end result in severe cases is colonization of the lungs with pathogenic bacteria resulting in severe pneumonia. *Pasteurella multocida, Haemophilus somnus* and *Mannheimia* (formerly *Pasteurella*) *haemolytica* are associated with bovine pneumonia.

However, *Mannheimia haemolytica* serotype 1(S1) is by far the most important and commonly isolated bacterial pathogen in development of the often-fatal fibrinous pleuropneumonia in beef cattle known as pneumonic pasteurellosis or "shipping fever".

Prevention and control of shipping fever in feedlots is currently partially addressed by three different mechanisms: antibiotic treatment upon arrival of cattle at the feedlot, antibiotic therapy for sick cattle, and vaccination against BRD viruses and *M. haemolytica*. The extensive use of antibiotics to control shipping fever increases the possibility of antibiotic residues in meat and the development of drug-resistant bacteria in cattle, including those bacteria with potential impact on human health such as *Salmonella* and *Escherichia coli* 0157:H7.

Viral and bacterial vaccines for the control of shipping fever have been used for many years. Despite their availability, the disease continues to be a major bovine health problem. Attempts to develop a vaccine include the following:

U.S. Pat. No. 5,055,400 to Lo et al., (Oct. 8, 1991) discloses the *Pasteurella haemolytica* leukotoxin gene and protein.

U.S. Pat. No. 5,476,657 (Potter, Dec. 19, 1995) and U.S. Pat. No. 5,871,750 (Potter, Feb. 16, 1991) disclose vaccines comprising *Pasteurella haemolytica* leukotoxin or truncated forms of the leukotoxin.

U.S. Pat. No. 5,708,155 (Potter et al., Jan. 13, 1998) and U.S. Pat. No. 6,797,272 (Potter et al., Sep. 28, 2004) disclose vaccines comprised of chimeras of *Pasteurella haemolytica* leukotoxin and an antigen such as somatostatin (SRIF), gonadotropin releasing hormone (GnRH), or rotavirus viral protein 4 (VP4).

U.S. Pat. No. 5,238,823 (Potter et al., Aug. 24, 1993), U.S. Pat. No. 5,273,889 (Potter et al., Dec. 28, 1993), U.S. Pat. No. 5,594,107 (Potter et al., Jan. 14, 1997) and U.S. Pat. No. 6,096,320 (Potter et al., 5 Aug. 1, 2000), disclose vaccines of chimeric proteins comprising *Pasteurella haemolytica* leukotoxin or an antigenic fragment thereof, and a cytokine such as gamma-interferon or interleukin-2.

U.S. Pat. No. 5,871,750 (Potter, Feb. 16, 1999) discloses vaccine compositions comprising a truncated *Pasteurella haemolytica* leukotoxin. Other *Pasteurella haemolytica* cell surface antigenic proteins are also disclosed (fimbrial protein, plasmin receptor protein, and 50K outer membrane protein.

U.S. Pat. No. 5,723,129 (Potter et al., Mar. 3, 1998), U.S. Pat. No. 5,837,268 (Potter et al., Nov. 17, 1998), U.S. Pat. No. 6,022,960 (Potter et al., Feb. 8, 2000) and U.S. Pat. No. 6,521,746 (Potter et al., Feb. 18, 2003) disclose vaccines comprised of chimeras of leukotoxin and gonadotropin releasing hormone (GnRH) multimers.

U.S. Pat. No. 6,475,754 (Bemis et al., Nov. 5, 2002) discloses an antigenic chimeric protein comprising fimbrial protein of *Bordetella bronchiseptica* and leukotoxin of *M. haemolytica*.

Immunity against *M. haemolytica* is thought to be primarily through production of serum antibodies that neutralize the secreted leukotoxin (LKT) and antibodies against surface antigens. The specific surface antigens that are important in stimulating host immunity to *M. haemolytica* are not known; however, several studies point towards the importance of outer membrane proteins (OMPs). Pandher et al. demonstrated 21 surface-exposed immunogenic outer membrane proteins in *M. haemolytica* S1 using protease treatment and Western blotting. (Pandher K, Murphy G L, Confer A W. Identification of immunogenic, surface-exposed outer membrane proteins of *Pasteurella haemolytica* serotype 1. Vet Microbiol 1999; 65: 215-26) High antibody responses to outer membranes, as measured by ELISA, and to several specific OMPs, as measured by quantitative Western Blotting, consistently correlated with resistance to challenge with virulent *M. haemolytica* S1 (Confer A W, McCraw R D, Durham J A, Morton R J, Panciera R J. Serum antibody responses of cattle to iron-regulated outer membrane proteins of *Pasteurella haemolytica* A1. Vet ImmunolImmunopathol 1995; 47: 101-10 and Mosier D A, Simons K R, Confer A W, Panciera R J, Clinkenbeard K D. *Pasteurella haemolytica* antigens associated with resistance to pneumonic pasteurellosis. Infect Immun 1989; 57: 711-6). Vaccination of cattle with OMP-enriched cellular fractions, from *M. haemolytica* S1 significantly enhanced resistance of cattle against experimental challenge in the absence of antibodies to LKT. (Morton R J, Panciera R J, Fulton R W, Frank G H, Ewing S A, Homer J T, Confer A W. Vaccination of cattle with outer membrane protein-enriched fractions of *Pasteurella haemolytica* and resistance against experimental challenge exposure. Am J Vet Res 1995; 56: 875-879) However, the extraction procedure for bacterial outer membranes is time consuming and expensive, making use of purified OMPs as a component of a *M. haemolytica* vaccine impractical due to cost. Thus, it can be appreciated that the identification of specific, surface exposed immunogenic *M. haemolytica* OMPs that would stimulate strong antibody responses is highly desirable. Cloning and expression of the appropriate gene(s) and production of recombinant OMP could then be achieved inexpensively.

One of the *M. haemolytica* OMPs to which high antibody responses correlated with resistance against experimental challenge is a major 45 kDa OMP. Prior studies were undertaken to clone and characterize that protein. In 1998, Pandher et al. reported the cloning, sequencing and characterization of the gene for the major 45-kDa *M. haemolytica* S1 outer membrane lipoprotein, designated PlpE. (Pandher K, Confer A W, Murphy G L. Genetic and immunologic analyses of PlpE, a lipoprotein important in complement-mediated killing of *Pasteurella haemolytica* serotype 1. Infect Immun 1998; 66: 5613-9, which publication is incorporated herein by reference) PlpE was found genetically to have 32-35% similarity to an immunogenic lipoprotein, OmlA, demonstrated in *Actinobacillus pleuropneumoniae* serotypes 1 and 5. Affinity-purified, anti-PlpE antibodies recognized an OMP in all serotypes of *M. haemolytica* except in serotype 11. In addition, PlpE was determined to be surface-exposed, and in complement-mediated killing assays, a significant reduction was observed in killing of *M. haemolytica* when bovine immune serum that was depleted of anti-PlpE antibodies was used as the source of antibody, suggesting that antibodies against PlpE may contribute to host defense against the bacterium.

Because of the economic constraints of the cattle industry, bovine vaccines must be low in cost. Therefore, current *M. haemolytica* vaccines are crude, usually consisting of a culture supernatant, which contains *M. haemolytica* leukotoxin and sloughed surface proteins, and/or the killed bacterium. Perino and Hunsaker reviewed published field studies on commercial *M. haemolytica* vaccines and found that efficacy could be established in only 50% of the trials. (Bov Practitioner 1997; 31: 59-66). There is thus an ongoing need for improvement in *M. haemolytica* vaccines, and for the development of improved methods and compositions for protecting cattle against shipping fever.

SUMMARY OF THE INVENTION

In connection with the present invention, the gene for *M. haemolytica* outer membrane protein PlpE was cloned and the recombinant PlpE (rPlpE) was purified and used in immunological and vaccination studies. It was discovered that adjuvanted rPlpE was highly immunogenic in cattle, and vaccination of cattle with 100 µg of rPlpE markedly enhanced resistance against experimental challenge with virulent *M. haemolytica*. It was also discovered that the addition of rPlpE to a commercial *M. haemolytica* vaccine significantly enhanced ($p<0.05$) protection afforded by the vaccine against experimental challenge.

Thus, in one aspect of the present invention there are provided vaccine compositions comprising rPlpE or conservatively modified variants thereof separately or which may optionally be combined with adjuvant to enhance the protection efficacy of vaccine preparations against BRD and/or shipping fever, wherein the vaccine composition further comprises a pharmaceutically acceptable carrier or diluent. The rPlpE also may optionally be combined with other immunogens and/or existing commercially available vaccines to form an augmented vaccine composition, wherein the vaccine composition further comprises a pharmaceutically acceptable carrier or diluent and adjuvant.

In another aspect of the invention there are provided methods for inducing an immune response in cattle to provide immune protection against BRD and/or shipping fever, the method comprising administering to an at-risk animal an effective amount of a vaccine composition comprising rPlpE or conservatively modified variants thereof alone or in combination with an adjuvant and/or other immunogens to provide a means to reduce the risk of BRD, wherein the vaccine composition further comprises a pharmaceutically acceptable carrier or diluent.

Most of the structure of an OMP molecule would play no significant role in inducing protective immune responses, because extended portions of the molecule are buried, unexposed, in the outer membrane. Instead, immunity can be attributed to only short, surface-exposed epitopes of these proteins. Identification of such surface-exposed epitopes as protective antigens in animal models has been the target of peptide vaccine design strategies for various pathogenic bacteria. Because of *M. haemolytica* PlpE's potential as an important immunogen, studies were undertaken to characterize surface-exposed and immunologically important epitopes of PlpE and to produce and test recombinant epitopes corresponding thereto. Thus, in another aspect of the invention there are provided immunologically important epitopes of rPlpE for use in vaccines and related methodologies.

In another aspect of the invention, chimeric proteins are provided which contain one or more copies of an immunodominant epitope of *M. haemolytica* rPlpE in combination with an immunodominant epitope of *M. haemolytica* leukotoxin.

The present invention provides an immunogenic composition which includes at least one chimeric protein comprising: one or more copies of an immunodominant epitope of recombinant *Mannheimia haemolytica* PlpE, and one or more copies of an immunodominant epitope of recombinant *Mannheimia haemolytica* leukotoxin (LKT); and a physiologically compatible carrier. In one embodiment, the immunodominant epitope of recombinant *Mannheimia haemolytica* PlpE is R2 and is represented by SEQ ID NO: 19. In one embodiment, the immunodominant epitope of recombinant *Mannheimia haemolytica* LKT is mLKT A and is represented by SEQ ID NO: 21. In one embodiment, the at least one chimeric protein further comprises a leader sequence, for example, the glutathione-S-transferase leader sequence. The at least one chimeric protein may further comprises one or more spacer peptides. In one embodiment of the invention, the at least one chimeric protein comprises two copies of the immunodominant epitope of recombinant *Mannheimia haemolytica* PlpE and two copies of the immunodominant epitope of recombinant *Mannheimia haemolytica* LKT.

The invention further provides a chimeric protein which comprises: one or more copies of an immunodominant epitope of recombinant *Mannheimia haemolytica* PlpE, and one or more copies of an immunodominant epitope of recombinant *Mannheimia haemolytica* leukotoxin (LKT). In one embodiment, the immunodominant epitope of recombinant *Mannheimia haemolytica* PlpE is R2 as represented by SEQ ID NO: 19. In one embodiment, the immunodominant epitope of recombinant *Mannheimia haemolytica* LKT is mLKT A as represented by SEQ ID NO:21. In another embodiment, the chimeric protein further comprises a leader sequence, which may be, for example, the glutathione-S-transferase leader sequence. In another embodiment, the chimeric protein comprises one or more spacer peptides. In one embodiment of the invention, the chimeric protein comprises two copies of the immunodominant epitope of recombinant *Mannheimia haemolytica* PlpE and two copies of the immunodominant epitope of recombinant *Mannheimia haemolytica* LKT.

The invention also provides a vaccine preparation which comprises at least one chimeric protein comprising: one or more copies of an immunodominant epitope of recombinant *Mannheimia haemolytica* PlpE, and one or more copies of an immunodominant epitope of recombinant *Mannheimia haemolytica* leukotoxin (LKT); and a physiologically compatible carrier. In one embodiment, the immunodominant epitope of recombinant *Mannheimia haemolytica* PlpE is R2 as represented by SEQ ID NO: 19. In one embodiment of the invention, the immunodominant epitope of recombinant *Mannheimia haemolytica* LKT is mLKT A as represented by SEQ ID NO: 21. In another embodiment, the at least one chimeric protein further comprises a leader sequence, one example of which is the glutathione-S-transferase leader sequence. In another embodiment, the at least one chimeric protein further comprises one or more spacer peptides. In other embodiments, the at least one chimeric protein comprises two copies of the immunodominant epitope of recombinant *Mannheimia haemolytica* PlpE and two copies of the immunodominant epitope of recombinant *Mannheimia haemolytica* LKT.

In yet other embodiments, the vaccine preparation of also includes an adjuvant.

The present invention also provides a method of eliciting an immune response to *Mannheimia haemolytica* in a mammal. The method comprises the step of administering to the mammal at least one chimeric protein comprising: one or more copies of an immunodominant epitope of recombinant *Mannheimia. haemolytica* PlpE, and one or more copies of an immunodominant epitope of recombinant *Mannheimia haemolytica* leukotoxin (LKT). In one embodiment, the immunodominant epitope of recombinant *Mannheimia haemolytica* PlpE is R2 as represented by SEQ ID NO: 19. In one embodiment of the invention, the immunodominant epitope of recombinant *Mannheimia haemolytica* LKT is mLKT A as represented by SEQ ID NO: 21. In another embodiment, the at least one chimeric protein further comprises a leader sequence, one example of which is the glutathione-S-transferase leader sequence. In another embodiment, the at least one chimeric protein further comprises one or more spacer peptides.

In another embodiment, the at least one chimeric protein comprises two copies of the immunodominant epitope of recombinant *Mannheimia haemolytica* PlpE and two copies of the immunodominant epitope of recombinant *Mannheimia haemolytica* LKT. In one embodiment of the invention, the mammal is bovine.

The invention also provides a method of vaccinating cattle to prevent or attenuate disease symptoms caused by *Mannheimia haemolytica*. The method comprises the step of administering to the cattle at least one chimeric protein comprising: one or more copies of an immunodominant epitope of recombinant *Mannheimia haemolytica* PlpE, and one or more copies of an immunodominant epitope of recombinant *Mannheimia haemolytica* leukotoxin (LKT). According to the method, the at least one chimeric protein is administered in an amount sufficient to prevent or attenuate disease symptoms caused by *Mannheimia haemolytica*. In one embodiment, the immunodominant epitope of recombinant *Mannheimia haemolytica* PlpE is R2 as represented by SEQ ID NO: 19. In one embodiment of the invention, the immunodominant epitope of recombinant *Mannheimia haemolytica* LKT is mLKT A as represented by SEQ ID NO: 21. In another embodiment, the at least one chimeric protein further comprises a leader sequence, one example of which is the glutathione-S-transferase leader sequence. In another embodiment, the at least one chimeric protein further comprises one or more spacer peptides In addition, in one embodiment, the at least one chimeric protein comprises two copies of the immunodominant epitope of recombinant *Mannheimia haemolytica* PlpE and two copies of the immunodominant epitope of recombinant *Mannheimia haemolytica* LKT.

A better understanding of the present invention, its several aspects, and its advantages will become apparent to those skilled in the art from the following detailed description, taken in conjunction with the attached figures, wherein there is described the preferred embodiment of the invention, simply by way of illustration of the best mode contemplated for carrying out the invention.

BRIEF DESCRIPTION OF THE DRAWINGS

FIG. 7 A-B. A, amino acid sequence of R2 immunodominant region (epitope) of rPlpE (SEQ ID NO: 19); B, DNA sequence encoding R2 (SEQ ID NO: 20).

FIG. 8 A-B. A, amino acid sequence of mLKTA (SEQ ID NO: 21); B, DNA sequence encoding mLKTA (SEQ ID NO: 22).

FIG. 10 A-B. A, amino acid sequence of SAC86 chimera (SEQ ID NO: 23). Sequences of spacer peptides are shown in italics; sequences from PlpE are shown in bold with a solid underline; and sequences from LKT are shown in bold with a dotted underline; B, nucleic acid sequence encoding SAC86 chimera (SEQ ID NO: 24).

FIG. 11 A-B. A, amino acid sequence of SAC87 chimera (SEQ ID NO: 25). Sequences of spacer peptides are shown in italics; sequences from PlpE are shown in bold with a solid underline; and sequences from LKT are shown in bold with a dotted underline; B, nucleic acid sequence encoding SAC87 chimera.(SEQ ID NO: 26).

FIG. 12 A-B. A, amino acid sequence of SAC88 chimera (SEQ ID NO: 27). Sequences of spacer peptides are shown in italics; sequences from PlpE are shown in bold with a solid underline; and sequences from LKT are shown in bold with a dotted underline; B, nucleic acid sequence encoding SAC88 chimera (SEQ ID NO: 28).

FIG. 13 A-B. A, amino acid sequence of SAC89 chimera (SEQ ID NO: 29); B, nucleic acid sequence encoding SAC89 chimera (SEQ ID NO: 30). For both A and B, sequences of spacer peptides are shown in italics; sequences from PlpE are shown in bold with a solid underline; and sequences from LKT are shown in bold with a dotted underline. FIA=Freund's Incomplete Adjuvant; TM=TiterMax®.

FIG. 14 A-B. A, amino acid sequence of SAC91 chimera (SEQ ID NO: 31). Sequences of spacer peptides are shown in italics; sequences from PlpE are shown in bold with a solid underline; and sequences from LKT are shown in bold with a dotted underline; B, nucleic acid sequence encoding SAC91 chimera (SEQ ID NO: 32).

FIG. 15 A-F. Data from endpoint titrations of mouse antibodies against rPlpE and LKTA. A, using 25, 50 or 75 μg of SAC86 and SAC87 proteins; B, using 25, 50 or 75 μg of SAC88 and SAC89 proteins.

FIG. 17 A-B. Quantification of Western blot data using densitometric analysis. A, blots against LKT; B, blots against PlpE.

FIG. 20 A-D. Antibody responses of cattle vaccinated with PBS plus adjuvant or 100 μg of SAC89 plus adjuvant. Data are expressed as nanograms of immunoglobulin binding to the antigen in ELISAs. A, antibodies to whole cells; B, antibodies to Leukotoxin; C, antibodies to PlpE; D, antibodies to SAC89.

DETAILED DESCRIPTION OF THE INVENTION

Figure 1:
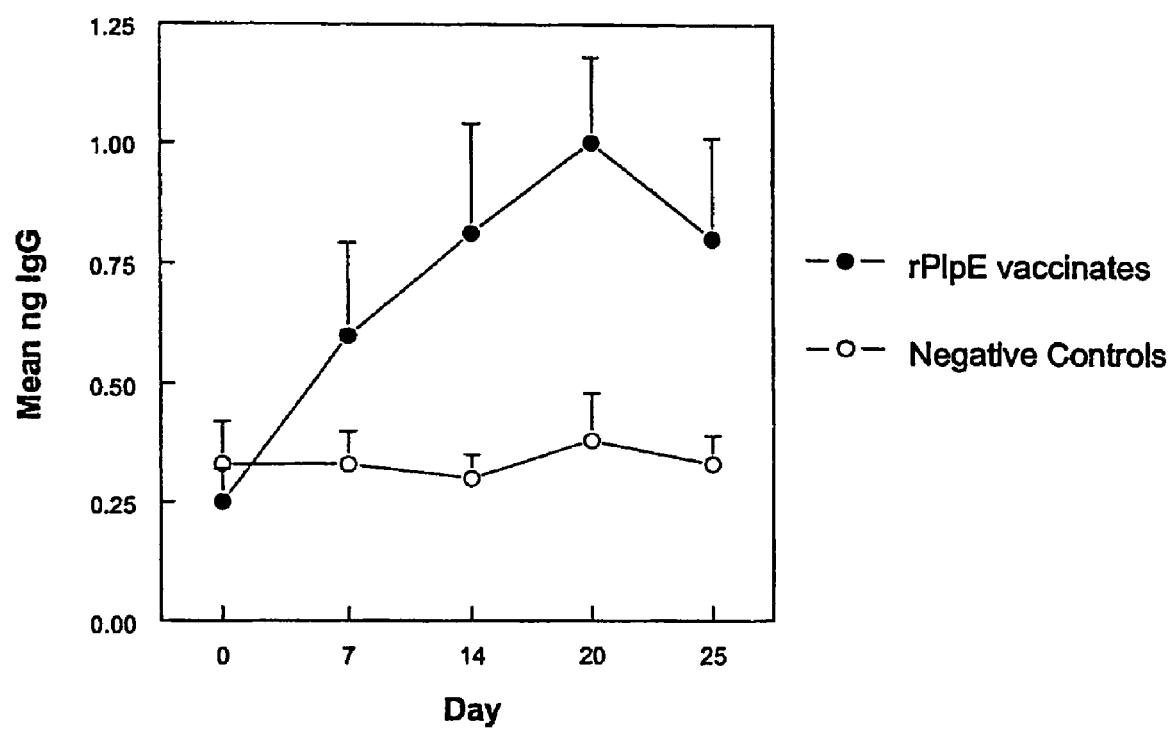
FIG. 1 is a graph depicting anti-PlpE antibody response of 6 cattle vaccinated with 100 μg of rPlpE on day 0.

The invention is not limited in its application to the details of the embodiments and steps described herein. The invention is capable of other embodiments and of being practiced or carried out in a variety of ways. It is to be understood that the phraseology and terminology employed herein is for the purpose of description and not of limitation.

In accordance with the present invention there are provided new vaccine preparations against BRD and shipping fever through the use of discrete recombinant PlpE and subunits of rPlpE containing immunoprotective regions. In one aspect, only rPlpE or immunoprotective and functional regions thereof are utilized as the antigenic component of the vaccine. In another aspect, rPlpE or subunits thereof are utilized in combination with other antigen components, such as leukotoxin (LKT).

In yet another aspect, the invention provides chimeras (both proteins and the nucleic acids that encode them) of the major surface-exposed epitope of PlpE (designated herein as either "E2" or "R2") and a minimal leukotoxin A fragment ("mLKTA"). In some embodiments, the chimeras include a leader sequence such as the GST leader sequence. In some embodiments, the antigenic regions (R2 and MLKTA) are present in multiple copies in the chimera., the multiple copies being separated by spacer peptides.

Another aspect of the present invention relates to methods useful to reduce the risk of BRD and shipping fever in cattle and prevent or attenuate biological transmission of the disease among cattle populations.

The experiments described and non-limiting examples provided hereinafter demonstrate that cattle immunized with rPlpE and/or epitopes thereof, or with chimeric proteins that include the immunodominant PlpE regions and mLKTA epitopes (particularly in multiple copies) are unexpectedly better protected against infection following challenge with *M. haemolytica* than cattle immunized with existing commercially available vaccines.

EXAMPLE 1

Immunogenicity of rPlpE and Vaccine Preparation

Studies were undertaken to determine the immunogenicity of outer membrane lipoprotein PlpE from *M. haemolytica* S1, to determine if commercial vaccines stimulate antibodies to it, and examine if addition of recombinant PlpE to a commercial *M. haemolytica* vaccine would augment vaccine-induced immunity.

1. Materials and Methods 1.1. Bacterial Culture.

*M. haemolytica* S1 Oklahoma Strain was used for serology antigen preparation and for challenge of animals. Frozen stock cultures were plated onto brain-heart infusion (BHI) and grown at 37° C. in a 5% $CO_2$ environment for 18 hours. An isolated colony from each was propagated in 10 ml BHI broth with rotatory shaking at 120 oscillations/min. for 18 hours at 37° C. 100 μl of suspension was added to 1 L of BHI broth and grown overnight. The bacteria were sedimented by centrifugation at 6000 ×g for 15 minutes, washed in 125 ml sterile phosphate buffered saline (PBS) and re-centrifuged as above 6000 ×g for 15 minutes. The bacteria were re-suspended in PBS and adjusted spectrophotometrically to a final concentration of approximately $1.0 \times 10^9$ CFU/ml (optical density of $A_{600}$=0.65).

1.2. Cloning and Purification of PlpE

The truncated form of plpE lacking the sequence encoding the putative signal peptide was amplified from pB4522 (Pandher et. al., 1998, supra) with the help of a forward primer starting 58 nucleotides into the 5'-end and priming into the open reading frame of plpE and a reverse primer which is complementary to the 3'-end of the gene. The amplimer was cut with BamHI and HindIII and ligated into an expression vector, pRSETA, cut with the same restriction enzymes. Competent *E. coli* DH5α were transformed with the ligation mixture and transformants were plated on Luria-Bertani (LB) agar plates with 50 μg/ml of ampicillin. Transformants were screened and appropriate subclones were identified. Plasmid DNA isolated from such subclones was submitted to the Oklahoma State University Core Facility where the nucleotide sequence was determined by the ABI Model 3700 (BioSciences) automated DNA sequencing system (SEQ ID NO: 1). Once the nucleotide sequence of a representative subclone was compared to that deposited in the GenBank (AF059036), the recombinant plasmid was introduced into BL21 (DE3) pLysS by transformation to express and purify rPlpE (SEQ ID NO: 2).

The expression of rPlpE was done according to the protocol recommended by the manufacturer of the vector and the expression host (Invitrogen, Calif.). Briefly, single colonies of BL21 (DE3) pLysS harboring the truncated plpE in pRSETA, were inoculated into appropriate volumes of LB broth with 50 μg/ml ampicillin and 34 μg/ml chloramphenicol. The culture was incubated at 37° C. until $A_{600}$=0.5 was attained at which time the synthesis of the recombinant protein was induced by adding IPTG (1 mM final concentration) and the induction was continued for at least 3 hours. In order to purify rPlpE, the culture was harvested and lysed by sonication. The cellular debris was then removed by centrifugation and the recombinant protein was loaded onto an affinity column packed by Pro-Bond nickel-chelating resin that selectively binds recombinant proteins with 6 histidine residues (His-Tag) at either the N- or carboxy-terminus. In this instance, the His-Tag is at the N-terminus. The recombinant protein bound to the resin was then eluted with either a low pH buffer or competition with imidazole.

The purity of each preparation was determined by SDS-PAGE followed by Coomassie stain and Western blot with murine anti-PlpE ascites fluid.

1.3.. Serology

Antibodies to formalin-killed *M. haemolytica* whole bacterial cells (WC), to LKT, and to rPlpE were determined by enzyme-linked immunosorbent assay (ELISA). For WC preparation, *M. haemolytica* S1 were prepared from a washed 24 hour culture by suspending cells in 0.4% formalinized saline at a concentration determined spectrophotometrically to be 1.850 $OD_{650}$. LKT was prepared from supernatant from a 3-hour culture of *M. haemolytica* S1 grown in RPMI-1640 medium at 37° C. in a shaking incubator. The LKT was partially purified by precipitation with 40-60% ammonium sulfate. The precipitate was resuspended in 3M guanidine containing 59 mM $NaHPO_4$ and 100 mM NaCl. By SDS-PAGE of the LKT preparation, one intensely staining band was identified at 105 kDa and confirmed to be LKT on a Western blot using an anti-LKT monoclonal antibody. Leukotoxic activity was $10^4$ LKT units per ml. The 2-keto-3-deoxyoctonate concentration was 7.5 µg per mg of protein.

Wells of 96-well microtiter plates were coated with WC at an optical density reading equivalent to $10^8$ CFU of a 24-hour culture, with LKT at 50 ng per well, or with rPlpE at 50 ng per well. Sera were diluted in PBS-Tween 20 containing 1% BSA. ELISA for detection of serum antibodies to PlpE was done in the first immunogenicity study using serum dilutions ranging from 1:400-1:819,200. Otherwise, sera were tested against various antigens at dilutions of 1:800 for WC, 1:1600 for LKT, and 1:1600 for rPlpE, which were in the linear range of established dilution curves. The extent of antibody binding was detected using a 1:400 dilution of horseradish peroxidase-conjugated, affinity purified rabbit anti-bovine IgG (Kirkegaard & Perry Laboratories, Gaithersburg, Md.). Antibody responses are expressed as ng of immunoglobulin binding based on a set of IgG standards on each plate.

1.4. Animals

A total of 82 normal healthy beef calves (Hereford or Angus/Hereford cross) of mixed sex were used. The calves were weaned at around 6-8 months of age. All calves were vaccinated with 7-way Clostridial vaccine and leptospiral vaccine, and treated with anthelmintic 30 days prior to the study. The calves received free choice native grass hay supplemented with grain ration throughout the study. All animal studies were done following using protocols approved the University Institutional Animal Care and Use Committee (Protocol #182).

1.5. Anti-PlpE Responses with *M. haemolytica* Vaccines

To determine if vaccination of cattle with commercial or experimental *M. haemolytica* vaccines stimulate anti-PlpE antibodies, two studies were done. The first experiment was a retrospective study using sera from 18 cattle from previous vaccine studies. Serum antibodies to PlpE were determined on samples from the day of vaccination (day 0) and from day 14. On day 0, three calves each were vaccinated subcutaneously with one of the following commercial vaccines: *P. haemolytica* Toxoid, BRSV-BVD-IBR-$PI_3$ Vaccine (PYRAMID™ 4/PRESPONSE®; Fort Dodge Laboratories), *P. haemolytica-multocida* Bacterin-Toxoid (PULMO-GUARD™ PH-M, Boehringer Ingelheim), *P. haemolytica-multocida-Salmonella typhimurium* Bacterin-Toxoid (POLY-BAC B® 1, Texas Vet Labs). Three calves were each vaccinated with 2 mg of an *M. haemolytica* outer membrane preparation in Freund's incomplete adjuvant or $10^9$ CFU of live *M. haemolytica*. In addition, sera were analyzed from three non-vaccinated calves that spontaneously seroconverted to *M. haemolytica* based on positive antibody responses to WC and LKT.

The second vaccine experiment was a prospective study designed to follow the anti-PlpE antibodies for 42 days after a single dose of a commercial *M. haemolytica* vaccine or rPlpE. Thirty calves were divided equally among 6 groups and vaccinated subcutaneously once each on day 0 with PRESPONSE®, *P. haemolytica* Bacterin-Toxoid (ONE SHOT™, Pfizer), an avirulent *M. haemolytica* culture (ONCE PMH®, Intervet), PULMO-GUARD™ PH-M, or 100 µg of rPlpE in commercial adjuvant (Pfizer). Five unvaccinated calves served as controls. Sera were obtained on days 0, 7, 14, 21, 28, and 42, and antibodies to WC, LKT and PlpE were determined.

1.6. Recombinant PlpE Immunogenicity Studies

To determine if rPlpE was immunogenic, one calf each was vaccinated once with either 10, 50, or 100 µg of rPlpE in a commercial proprietary adjuvant (Pfizer Inc, Lincoln, Nebr.). One calf remained as a non-vaccinated control. Sera were obtained 21 days after vaccination and evaluated for end-point antibody titers against rPlpE using serial 2-fold dilutions. Twenty-four days after the initial vaccination, each calf and a non-vaccinated calf were transthoracically challenged with $5.0 \times 10^9$ CFU of live *M. haemolytica* from an overnight culture in accordance with established procedures. Four days later, calves were humanely killed, and lung lesion scores determined on a 20-point scale.

In a second cattle experiment, 6 cattle were vaccinated with 100 µg of rPlpE in commercial adjuvant on day 0 and 6 calves remained as non-vaccinated controls. On day 21, all cattle were challenged intrathoracically with $1 \times 10^9$ CFU of virulent *M. haemolytica*. Calves were humanely killed on day 25, and lung lesion scores determined. Antibody responses against rPlpE and *M. haemolytica* WC were determined on days 0, 7, 14 and 21 after vaccination.

In a third cattle experiment, PRESPONSE® was obtained from the manufacturer, and 18 weanling beef steers were equally allocated among the following vaccine groups: Group 1-PRESPONSE, Group 2-PRESPONSE+100 µg PlpE, and Group 3-non-vaccinated. Cattle were vaccinated on day 0 with 2 ml of PRESPONSE (manufacturer's recommended dosage) or 2 ml of PRESPONSE mixed with 0.5 ml of PlpE (100 µg). Antibody responses to *M. haemolytica* WC, rPlpE or to LKT were determined by ELISA on days 0, 7, 15, and 23. On day 24, cattle in Groups 1, 2, & 3 were challenged transthoracically with $3.0 \times 10^9$ CFU of *M. haemolytica*. Four days later, calves were humanely killed, and lung lesion scores determined.

1.7. Statistical Analysis

Mean rectal temperatures, antibody responses and lesion scores among the various groups were compared by Students t tests. Mean rectal temperatures and antibody responses within groups were compared by paired t tests. Differences were considered significant when p<0.05. Linear regression analyses were done to determine if there was a significant correlation between antibody response and lesion score.

2. Results 2.1. Recombinant PlpE Immunogenicity

In the first immunogenicity experiment that determined end-point anti-rPlpE titers in response to various doses of rPlpE, serum from the non-vaccinated calf had an end-point antibody titer of 1:400 against rPlpE. Sera from the 10, 50, and 100 µg vaccinates had titers of 1: 12,800, 1: 25,600, and 1: 25,600, respectively. Intrathoracic challenge of those calves with virulent *M. haemolytica* resulted in a lesion score of 15.5 (20 maximum severity) for the non-vaccinated control calf. Lesion scores for the 10, 50, and 100 µg-vaccinates were 4.5, 3.0, and 3.5 respectively.

In the second immunogenicity experiment, vaccination with rPlpE on day 0 stimulate a significant increase in antibodies to rPlpE and to *M. haemolytica* WC on day 7 (FIG. 1). Those responses continued to increase to a maximum on day 20 and declined insignificantly on day 25, whereas antibodies to rPlpE and to WC failed to increase for the nonvaccinated calves.

Anti-LKT antibodies did not significantly increase for either the rPlpE-vaccinated or control groups (data not shown). Mean lesion scores (standard deviation) after challenge were 7.0+3.8 for nonvaccinated controls and 4.1±3.0 for the rPlpE vaccinates, a 41.4% reduction in lesion scores. Those differences were significant at the level of p=0.07. When data from the first experiment were combined with these data, the mean lesion score for nonvaccinated controls was 8.2±4.7 and mean lesion score for PlpE vaccinates was 3.9±2.6 (p<0.05), a 52.1% reduction in lesion scores.

2.2. *M. haemolytica* Vaccines

Figure 2:
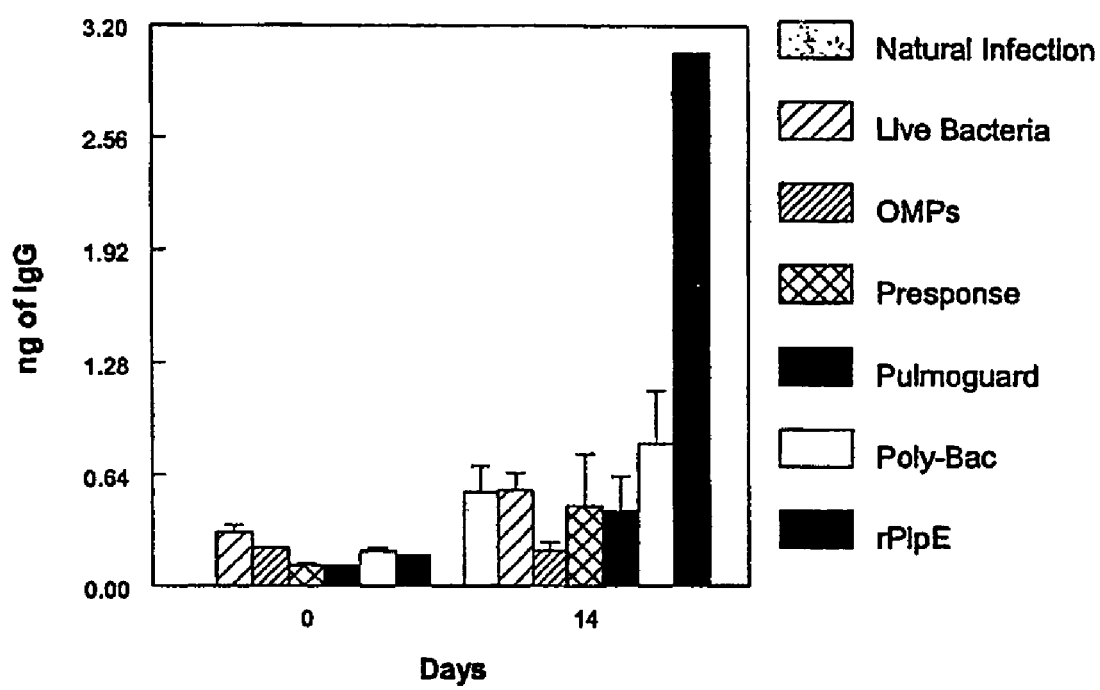
FIG. 2 is a bar graph depicting anti-PlpE antibody responses of cattle that spontaneously seroconverted to *M. haemolytica* (Natural Infection), vaccinated with commercial vaccines, *M. haemolytica* outer membranes (OMP), or live *M. haemolytica*.

In the first vaccine experiment, vaccination of calves with commercial vaccines, *M. haemolytica* outer membranes, and live *M. haemolytica* resulted in a nonsignificant increase in antibodies to PlpE (FIG. 2). In contrast, natural exposure to *M. haemolytica*, as indicated by spontaneous seroconversion, resulted in a significant increase in anti-PlpE antibodies. All vaccine-induced responses and natural exposure were substantially less than the antibodies produced in a calf vaccinated with 100 µg of rPlpE in commercial adjuvant. There were no significant differences among the antibody responses to rPlpE on day 14 for any of the commercial vaccine, live *M. haemolytica* vaccinated, or natural exposure groups. Antibody responses to *M. haemolytica* LKT and WC significantly increased for PULMOGUARD- and the live bacteria-vaccinated and natural exposure calves, whereas vaccination with outer membranes stimulated a significant antibody response to WC and vaccination with POLY-BAC and PRESPONSE failed to stimulate significant antibody responses to either *M. haemolytica* antigen (data not shown).

Figure 3:
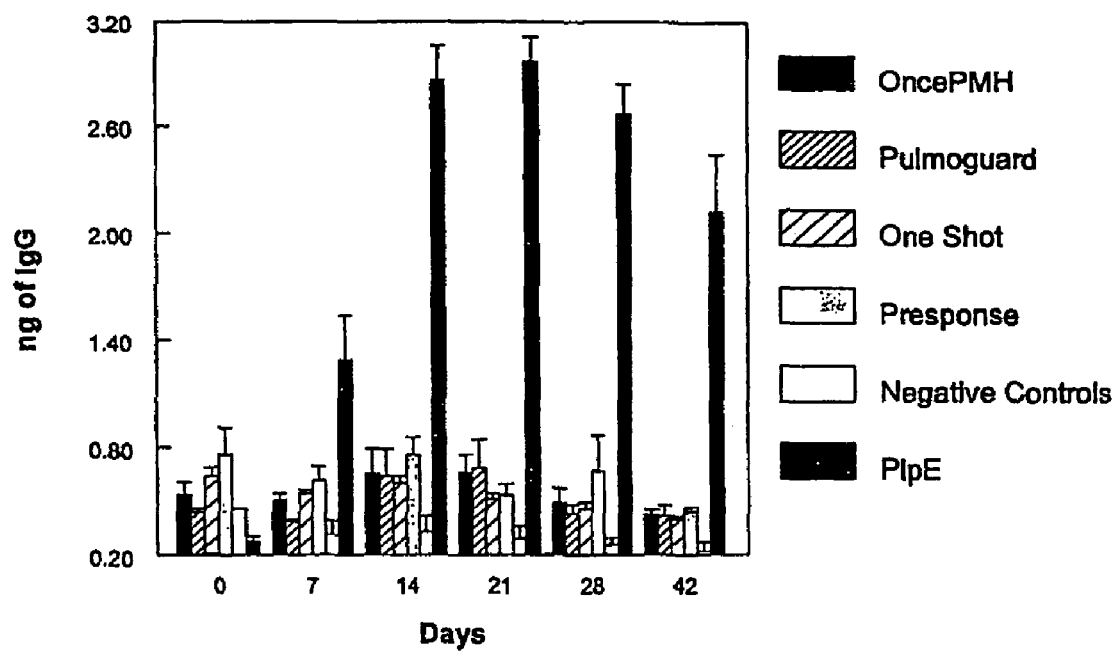
FIG. 3 is a bar graph depicting anti-PlpE antibodies for cattle vaccinated with commercial *M. haemolytica* vaccines or 100 μg of rPlpE.

In the second vaccine experiment, vaccination of calves with one of four commercial *M. haemolytica* vaccines resulted in nonsignificant increases in antibodies to PlpE (FIG. 3).

Vaccination of calves with 100 µg of rPlpE in commercial adjuvant stimulated a significant increase in antibody responses to PlpE by day 7. That response continued to increase until it peaked on day 21 after vaccination. Vaccination with each commercial vaccine and with rPlpE resulted in significant increases in antibodies to *M. haemolytica* WC by day 7 (ONE SHOT and PRESPONSE) and by day 14 (ONCE PMH, PULMOGUARD, and rPlpE) (FIG. 2). Those responses remained significantly increased through day 14 (ONCE PMH and PRESPONSE) and day 42 (ONE SHOT, PULMOGUARD, and rPlpE). Peak antibody responses for ONE SHOT-vaccinated cattle were significantly greater than peak responses for ONCE PMH, PRESPONSE or rPlpE vaccinates. Although antibody responses to LKT increased after vaccination with each commercial vaccine, only the responses initiated by PULMOGUARD and ONE SHOT were significantly increased beginning on day 7 through day 28. Anti-LKT antibodies did not increase for the rPlpE vaccinates. Peak anti-LKT antibody responses for PULMOGUARD-vaccinated cattle were significantly greater than peak responses for ONCE PMH, PRESPONSE or rPLpE vaccinates, whereas peak anti-LKT antibody responses for ONE SHOT-vaccinated cattle were significantly greater than peak responses for PRESPONSE vaccinates.

2.3. Augmentation of Commercial Vaccine with rPlpE

Figure 4A:
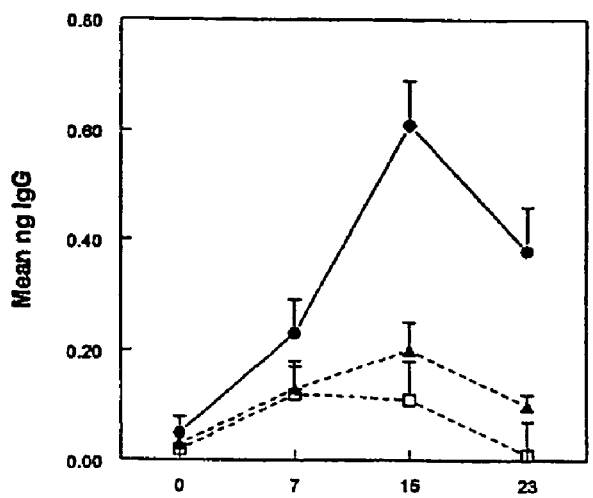
FIG. 4 A-C is a series of graphs depicting anti-PlpE (A), anti-*M. haemolytica* leukotoxin (B), and anti-*M. haemolytica* whole cells (C) in cattle vaccinated with PRESPONSE, PRESPONSE plus 100μg of rPlpE, or nonvaccinated.
Figure 4B:
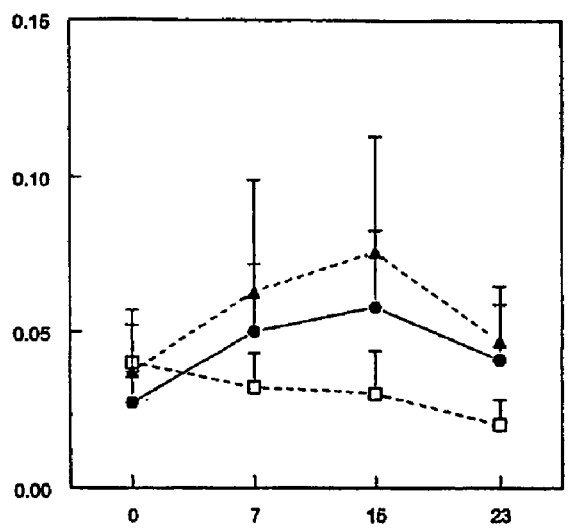
Figure 4C:
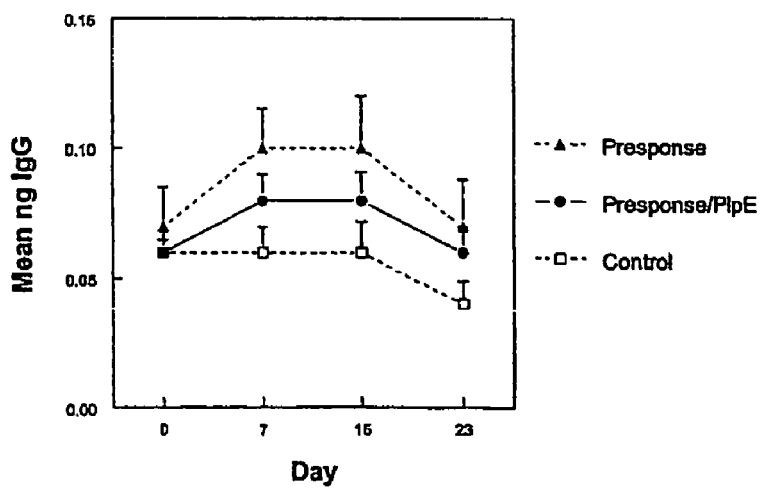

Because vaccination with commercial *M haemolytica* vaccines stimulated low antibody responses to rPlpE, we investigated the augmentation of a commercial vaccine with rPlpE. Vaccination with PRESPONSE stimulated a significant increase in anti-rPlpE antibodies on day 15. Those responses, however, were not significantly different than were antibody responses of the nonvaccinated control calves on days 7, 15, and 23 (FIG. 4 A-C). PRESPONSE-rPlpE vaccination stimulated a significant increase in anti-rPlpE antibodies on days 7, 15 and 23, and those responses were significantly higher than responses for the PRESPONSE-vaccinated or nonvaccinated control calves. Anti-WC and anti-LKT responses were significantly increased on days 7 and 15 for the PRESPONSE- and PRESPONSE-rPlpE vaccinates. Those responses were not significantly different between those groups, whereas they were significantly greater than were anti-WC and anti-LKT antibody values for the nonvaccinated control group.

Figure 5:
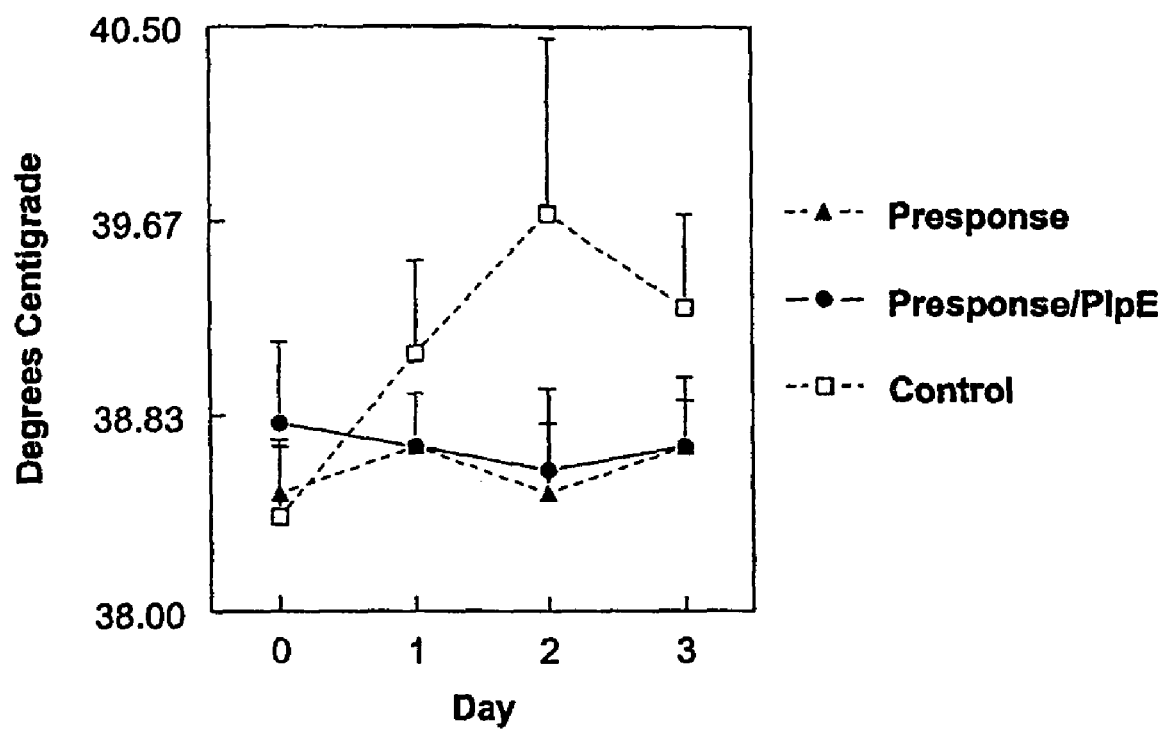
FIG. 5 is a graph depicting rectal temperatures of calves after challenge.

Rectal temperatures were taken on the day of challenge (day 24) and for the next 3 days (FIG. 5). Rectal temperatures remained essentially normal for all cattle except for the non-vaccinated Control group. In that group, rectal temperatures significantly increased on days 25 and 26, declining insignificantly on day 27. On days 26 and 27, mean rectal temperatures for the nonvaccinated Control group were significantly greater than for either the PRESPONSE or PRESPONSE/rPlpE groups. At necropsy, mean lung lesion scores were 7.9±3.6 for nonvaccinated controls, 3.0±1.3 for PRESPONSE-vaccinates (62.0% reduction in lesion score), and 1.1±0.9 for PRESPONSE/rPlpE vaccinates (86.1 % reduction in lesion scores). Differences between the PRESPONSE and Control and PRESPONSE/PlpE and Control lesion scores were significant. In addition, mean lesion score for the PRESPONSE/PlpE group was significantly lower than for the PRESPONSE group. There was a significant correlation ($r=-0.598$, $p<0.01$) between high serum antibody responses to rPlpE at day 23 and low lesion scores.

3. Discussion

The foregoing studies demonstrate that rPlpE is highly immunogenic for cattle and that vaccination with rPlpE can greatly enhance resistance against experimental challenge with the bacterium. The in vivo studies definitively indicate that anti-PlpE antibodies can contribute to host defense against *M. haemolytica* infection.

Vaccination of cattle with commercial *M. haemolytica* vaccines, live *M. haemolytica* or outer membranes or after prior natural exposure stimulated low antibody responses to PlpE. For those vaccines, the rise in antibodies to rPlpE as measured on various days were not significant, and even those vaccines that stimulated high antibodies to *M. haemolytica* WC and LKT still stimulated low anti-rPlpE response. Commercial vaccine-induced anti-rPlpE antibody responses were substantially lower than those stimulated by vaccination with 100 μg of rPlpE in a commercial adjuvant. This was not unexpected, because commercial vaccines vary greatly in their composition in that some are composed of culture supernatants and bacterial cell components, others contain whole bacterial cells, and one is a live mutant. A somewhat surprising finding was that calves previously vaccinated with *M. haemolytica* outer membranes in Freund's incomplete adjuvant had low antibody responses to rPlpE on day 14 (see Morton et al., supra). Therefore, although PlpE is a major outer membrane protein, its concentrations in commercial and experimental vaccines are most likely low and variable. In addition, the adjuvant used may play an important role in stimulating antibodies to PlpE.

Because commercial vaccines stimulated low antibodies to PlpE, we used rPlpE to augment the antibody response of a commercial vaccine, PRESPONSE, and demonstrated that PRESPONSE/PlpE stimulated greater protection against challenge than did PRESPONSE alone. Conlon et al. previously demonstrated that addition of recombinant LKT enhanced the efficacy of a culture supernatant vaccine and decreased clinical signs and pneumonic lesions. (Conlon J A, Shewen P E, Lo R Y. Efficacy of recombinant leukotoxin in protection against pneumonic challenge with live *Pasteurella haemolytica* A1. Infect Immun 1991; 59:587-91) Therefore, addition of one or more recombinant proteins to a *M. haemolytica* vaccine could be used by animal health companies to provide better products for protection of cattle against shipping fever.

In a recent survey, researchers found that of the *M. haemolytica* isolates from bovine respiratory disease from upper Midwestern United States were 60% A1, 26% A6 and 7% A2 with the remaining isolates from A9, A11 and untypable strains.(Al-Ghamdi G M, Ames T R, Baker J C, Walker R, Chase C C, Frank G H, Maheswaran S K. Serotyping of *Mannheimia (Pasteurella) haemolytica* isolates from the upper Midwest United States. J Vet Diagn Invest 2000; 12: 576-8) In another study, 60% of *M. haemolytica* isolates from cattle in a Texas feedyard were A1, whereas 40% were serotypes A2, A6, or A5 (Purdy C W, Raleigh R H, Collins J K, Watts J L, Straus D C. Serotyping and enzyme characterization of *Pasteurella haemolytica* and *Pasteurella multocida* isolates recovered from pneumonic lungs of stressed feeder calves. Curr Microbiol 1997; 34: 244-9). Therefore, although serotype 1 is the most common isolate from shipping fever, other serotypes play a role in the disease. Currently available *M. haemolytica* vaccines contain serotype 1 exclusively and therefore may or may not provide efficacious immunity against other serotypes. Cross serotype protection as stimulated by outer membrane vaccines or bacterins is limited. It is known that antibodies against *M. haemolytica* serotype 1 LKT will cross neutralize the toxin prepared from other serotypes. Therefore, commercial vaccines that stimulate anti-LKT antibodies should provide some cross protection against other serotypes.

However, Conlon et al. (supra) demonstrated that vaccination with recombinant LKT alone failed to stimulate protection against experimental *M. haemolytica* challenge, and Purdy et al (Purdy C W, Straus D C, Struck D, Foster G S. Efficacy of *Pasteurella haemolytica* subunit antigens in a goat model of pasteurellosis. Am J. Vet res 1993; 54:1637-47) found that vaccination of goats with LKT-impregnated agar beads stimulated incomplete immunity. Shewen and Wilkie (Shewen P E, Wilkie B N. *Vaccination of calves with leukotoxic culture supernatant from Pasteurella haemolytica*. Can J Vet Res 1988; 52:30-6) demonstrated that immunity to *M. haemolytica* was directed against both surface antigens and LKT. The actual surface antigen of importance in stimulating protections is not known for sure; however, studies indicate that is it most likely outer membrane proteins and not capsular polysaccharide or lipopolysaccharide. Pandher et al. (Supra) demonstrated the presence of a PlpE—like protein in outer membrane of all *M. haemolytica* serotypes except serotype 11, an uncommon isolate from shipping fever. There was some variation in molecular masses among the various proteins. With the current findings, demonstrating immunogenicity of rPlpE and augmentation of a commercial vaccine that stimulates anti-LKT antibodies, the previous demonstration of a PlpE—like protein in most serotypes and the at anti-LKT antibodies can neutralize LKT from other serotypes, the addition of rPlpE to a commercial vaccine that stimulates anti-LKT antibodies will enhance cross serotype protection in shipping fever.

EXAMPLE 2

Characterization of rPlpE epitopes

Additional studies were undertaken to characterize surface-exposed and immuologically important epitopes of rPlpE.

1. Materials and Methods 1.1 Construction and Purification of Truncated Forms of rPlpE Three additional rPlpE proteins carrying varying degrees of deletions were constructed in pET28 and purified according to the method described above. The first of these was obtained by using plpBM-1 (5'-CTTGGATCCCAAGCA-CAAAATGTT-3') (SEQ ID NO: 3), a primer that primes 84 bp into the 5' end of plpE thus introducing a deletion of 28 amino acids into the N-terminus end of rPlpE (rPlpEAN28); and the second by plpBM-2 (5'-CCTGGATCCCAAGCA-GAGGTTACT-3') (SEQ ID NO: 4), which primes 228 bp into the 5' end of plpE introducing a 76 amino acid deletion in the N-terminus of rPlpE (rPlpEAN76); and the third with plpBM-3 (5'-ATTGGATCCAATGCTGAACAACTC-3') (SEQ ID NO: 5) that primes 450 bp into 5' end of plpE introducing a deletion of 150 amino acids into the N-terminus in of rPlpE (rPlpEAN150). The reverse primer in all instances was plpEER, (5'-GACTGAATTCT-TATTTTTTCTCGCTAACCATTA-3') (SEQ ID NO: 6).

1.2. Production of Polyclonal Mouse Ascites

Three female, CFW mice were immunized 3 times with 50 μg of complete or truncated rPlpE diluted by half in RIBI (Corixa Corp, Seattle, Wash.) adjuvant. The first immunization was done subcutaneously (SC). Subsequent immunizations were done intraperitoneally (IP). A test-bleed was performed and the serum screened for antibodies to rPlpE by ELISA. The response was moderate, so two additional immunizations were performed IP. The mice were then injected with approximately 2×106 sarcoma cells (ATCC cat # TIB-66). Between 7 and 10 days after sarcoma injection, the mice started producing ascites. Ascites fluid was removed from each mouse three times; mice were then euthanized by barbiturate overdose.

1.3. Preparation of Affinity Columns and Purification of Anti-PlpE Antibodies

Purified rPlpE was coupled to NHS-activated SEPHAROSE™ 4 Fast Flow (Amersham Biosciences, Upsala, Sweden) according to the manufacturer's recommendation. Briefly, 3-7 mg of rPlpE in PBS was mixed with 2 ml bed volume of washed and equilibrated NHS-activated SEPHAROSE™ 4 Fast Flow in an Econo Column (BioRad, Hercules, Calif.), incubated at 4° C. overnight at which time the non-reacted groups were blocked by 0.1 M Tris pH 8.0, and washed with alternating high and low pH buffers, Tris, pH 8.0 and acetate buffer pH 4.0, respectively.

Several affinity columns were prepared with rPlpE carrying varying degrees of truncation from the N-terminus.

Anti-rPlpE antibodies against specific regions of PlpE were purified using the affinity columns described above. The Econo-Column with NHS-activated SEPHAROSE™ coupled to an rPlpE of interest was fitted with a Flow adaptor according to the recommendation of the manufacturer (Bio-Rad, Hercules, Calif.). The affinity column was equilibrated by applying Dulbecco's Phosphate Buffered Saline (DPBS) at a flow rate of 1 ml/min. Hyperimmune serum produced by immunizing calves with the intact rPlpE was mixed with DPBS in a ratio of 1 to 10 and passed through Nalgene 0.45 μm PES filters (Nalge, Rochester, N.Y.). The filtered serum was then applied to the equilibrated column via peristaltic pump at a flow rate of 1 ml/min. The flow thru was re-applied to the column several times to re-extract the serum by connecting the flow through to the reservoir of the initial serum. The column was then washed with DPBS. The complete removal of nonspecific proteins was determined with the help of the UV monitor attached to a chart recorder. Once there was no indication of nonspecific protein in the flow through, the specifically bound antibody was eluted with 100 mM Glycine Buffer (100 mM Glycine, 140 mM NaCl, pH 3.0) by collecting fractions in microfuge tubes containing 1/10 vol of 1 M Tris-HCl, pH 8.0. The absorbance of each fraction was determined at 280 nm. Those fractions that had a reading at least 2-3 times the background were pooled and dialyzed overnight against DPBS at 4° C. in a Slide-A-Lyzer® Dialysis Cassette (Pierce, Rockford, Ill.). The concentration of affinity purified antibody was determined with BCA Protein Assay Kit (Pierce, Rockford, Ill.). More specific antibodies against rPlpE with 28, 76 and 150 amino acids deletions on their N-termini, rPlpEΔN28 (pSAC63), rPlpEΔN76 (pSAC64) and rPlpEΔN150 (pSAC65), respectively, were purified as described.

Antibodies against regions of PlpE that are exposed on the surfaces of *M. haemolytica* cells were purified as described by Turbyfill et al., (1998). Briefly, intact *M haemolytica* cells from the late log phase were incubated with hyperimmune bovine sera immunized by rPlpE or anti-PlpE mouse ascites diluted in PBS on ice for 2-4 hr with gentle agitation. The cells were spun down and washed several times with PBS. The antibodies bound to the surface were eluted by resuspending and agitating the cells in 0.1M Glycine, 140 mM NaCl, pH 3.0 for at least 30 minutes. The cells were centrifuged at 13,000× g, and the eluted antibodies were collected in the supernatant which was neutralized immediately by adding 1/10 volume of 1 M Tris, pH 8.0.

1.4. Epitope Mapping of PlpE by Peptide Array (Pepscan)

A peptide array comprising a total of 109 overlapping 13-mer peptides with 3 amino acid offsets was custom made by Sigma-Genosys LP (The Woodlands, Tex.). Briefly the synthesis of peptides was performed on cellulose membranes in which hydroxyl functions of a commercially available filter paper are derivatized with 9-fluorenylmethoxycarbonyl-B-alanine (Fmoc-B-A1a) with subsequent removal of the Fmoc group. The synthesis areas were defined by spotting a Fmoc-B-alanine-pentafluorophenyl ester solution to distinct areas on the membrane. Blocking the remaining amino functions between spots provided discrete reaction sites on the membrane for further standard solid phase peptide synthesis using amino acid pentafluorophenyl esters. Peptides remained covalently attached to the cellulose membrane by the C-terminus and have a free N-terminus.

The peptide array was probed with anti-PlpE hyperimmune sera as follows. Prior to blotting, membranes with the custom spots were blocked with SuperBlock® Dry Blend (Pierce, Rockford, Ill.) blocking buffer in TBS, pH 7.4. The membrane was then incubated in blocking buffer containing a primary antibody at a dilution of 1:1000 to 1:5000 for an hour. Following several washes with TBS, pH 7.4, supplemented with 0.05% Tween-20,0. 2% Triton®-X-100 (TBSTT), the membrane was incubated in Superblock containing a goat anti-bovine or anti-mouse secondary antibody conjugated to Horse Radish Peroxidase (KPL, Gaithsburg, Md.) at dilutions 1:100,000 to 1:200,000 for one hour. The membrane was washed several times with TBSTT. The peptide array was incubated with SuperSignal® West Pico Chemiluminescent Substrate working solution (0.125 ml/$cm^2$) for 5 minutes, placed in plastic membrane protector and exposed to a CL-X POSURE™ (Pierce, Rockford, Ill.) X-Ray film for varying durations of time. The X-Ray film was then developed in a Konica SRX-101A Medical Film Processor (Taiwan). The developed X-Ray film was scanned by Arcus 1200 Agfa scanner (Taiwan), and scanned images were analyzed using Gene Pix® Pro 4.0 (Axon Instruments, Union City, Calif.). Signal intensities were defined as median pixel intensity following subtraction of local median background signal. The peptide array was stripped with RESTORE™ Western Blot Stripping Buffer (Pierce, Rockford, Ill.) according to the procedure recommended by the manufacturer before it was probed with a different anti-PlpE antibody. This was repeated several times with anti-PlpE antibodies obtained from different sources or purified in varieties of ways.

2. Results 2.1. Epitope Mapping of PlpE

The determination of the epitope map of PlpE was attempted in two steps. The first approach involved the localization of the general area of immunogenic or immunodominant epitopes by deleting specific regions of PlpE from both the N-Terminus and C-Terminus by PCR with the help of specific primers. A total of 6 plasmid constructs carrying the plpE gene with varying degrees of deletions were made. The cloning of three of these constructs that carry deletions from the N-termini of PlpE, (pSAC63, pSAC64, and pSAC65) is described above. Three additional plasmids viz., pSAC30, pSAC31, and pSAC32 that carry 106(rPlpEAC106), 96(rPlpEAC96) and 86(rPlpEAC86) amino acid deletions on the C-terminus of PlpE, respectively, were designed and constructed. The reverse primers used to introduce these deletions on the 3' end of the plpE gene in the latter constructs were HNplp-1 (5'-GATAAGCTTTTACCGTGCGGCAAATTC-3') (SEQ ID NO: 7), Hnplp-2(5'-AAAAAGCTITTATTTAATTTCTACATC-3') (SEQ ID NO: 8), and HNplp-3 (5'-TTTAAGCTTTTATATACTTCCTTGAGC-3') (SEQ ID NO: 9), respectively, and a forward primer plpEBH, (5'-GTCAGGATCCTGCGGAGGAAGCGGTAGC-3') (SEQ ID NO:

10). Amplimers were cut with BamHI and HindIII and cloned into pET28 or pRSETA cut with the same enzymes. Following confirmation of the identity of putative clones by both restriction analysis and sequencing, plasmids from true clones were introduced into BL21 (DE3) by transformation where the truncated forms of PlpE were overexpressed and purified according to the protocol described earlier. The 6 truncated forms of rPlpE and the intact form were separated on a 12.5% SDS-PAGE for Western analysis. Hyperimmune serum from calves immunized with the intact rPlpE was used as primary antibodies and goat anti-bovine alkaline Phosphatase conjugated antibodies as secondary antibodies. Densitometric analysis of the respective bands in a Western blot in which the same amount of the recombinant proteins were loaded onto an SDS-PAGE and probed with hyperimmune serum from a calf that was immunized with rPlpE clearly showed that there are significant differences amongst recombinant proteins carrying deletions in the intensity of their reaction to the hyperimmune serum. Accordingly there is no difference in the intensity of binding between rPlpE and mutants with the deletions from the C-terminus viz., pSAC30, pSAC31, and pSAC32 that carry 106 (rPlpEΔC106), 96 (rPlpEΔC96) and 86 (rPlpEΔC86) amino acid deletions on the C-terminus of PlpE, respectively. The binding capacity of mutants carrying deletions on their N-termini decreases with increasing deletions. There is no appreciable difference between rPlpE and pSAC63 (rPlpEΔN28) with 28 amino acid deletions on the N-terminus. The reactivity of pSAC64 (rPlpEΔN76), which carries a deletion of 76 amino acids on the N-terminus, drops to 63%, which is a 37% loss in signal intensity, when compared to rPlpE. Further deletion into the N-terminus as seen in pSAC65 (rPlpEΔN150) reduces the binding capacity of the truncated proteins by 60%. These findings clearly suggest that the region between residues 28 and 76 from the N-terminus of PlpE carries a stretch of amino acids with possible epitope(s) that may be responsible for invoking the immune response elicited when rPlpE is used as a vaccine.

2.2. Fine Mapping of Epitopes on PlpE

Figure 6:
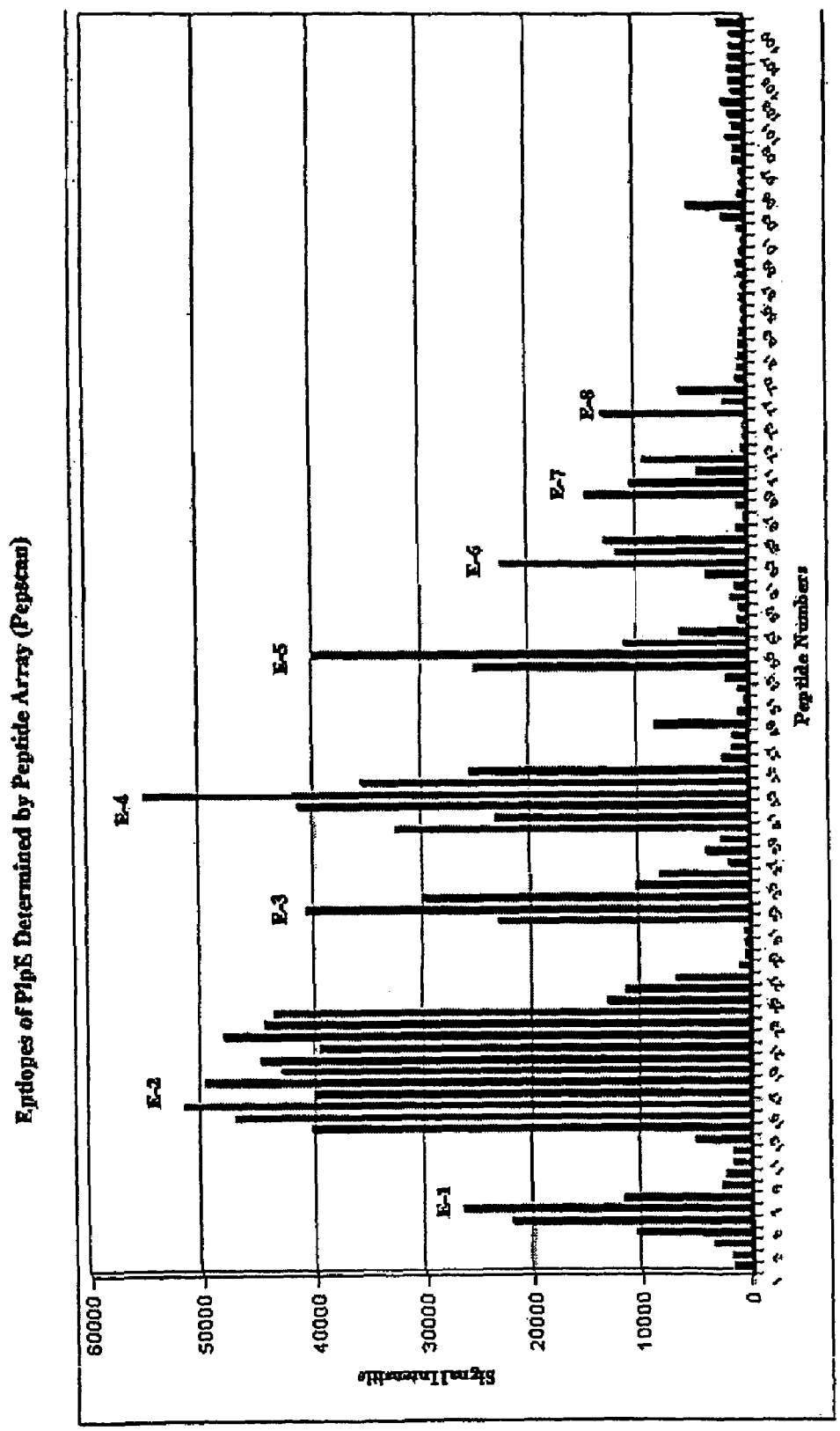
FIG. 6 is a graphical depiction of bovine antibody against surface exposed components of PlpE that was affinity purified with intact *M. haemolytica* cells and used to probe a peptide array. Densitometric analysis demonstrated a total of 8 distinct antigenic regions (E1-8) in PlpE with E2 being the largest and E4 having the highest densitometric signal.
Figure 9F:
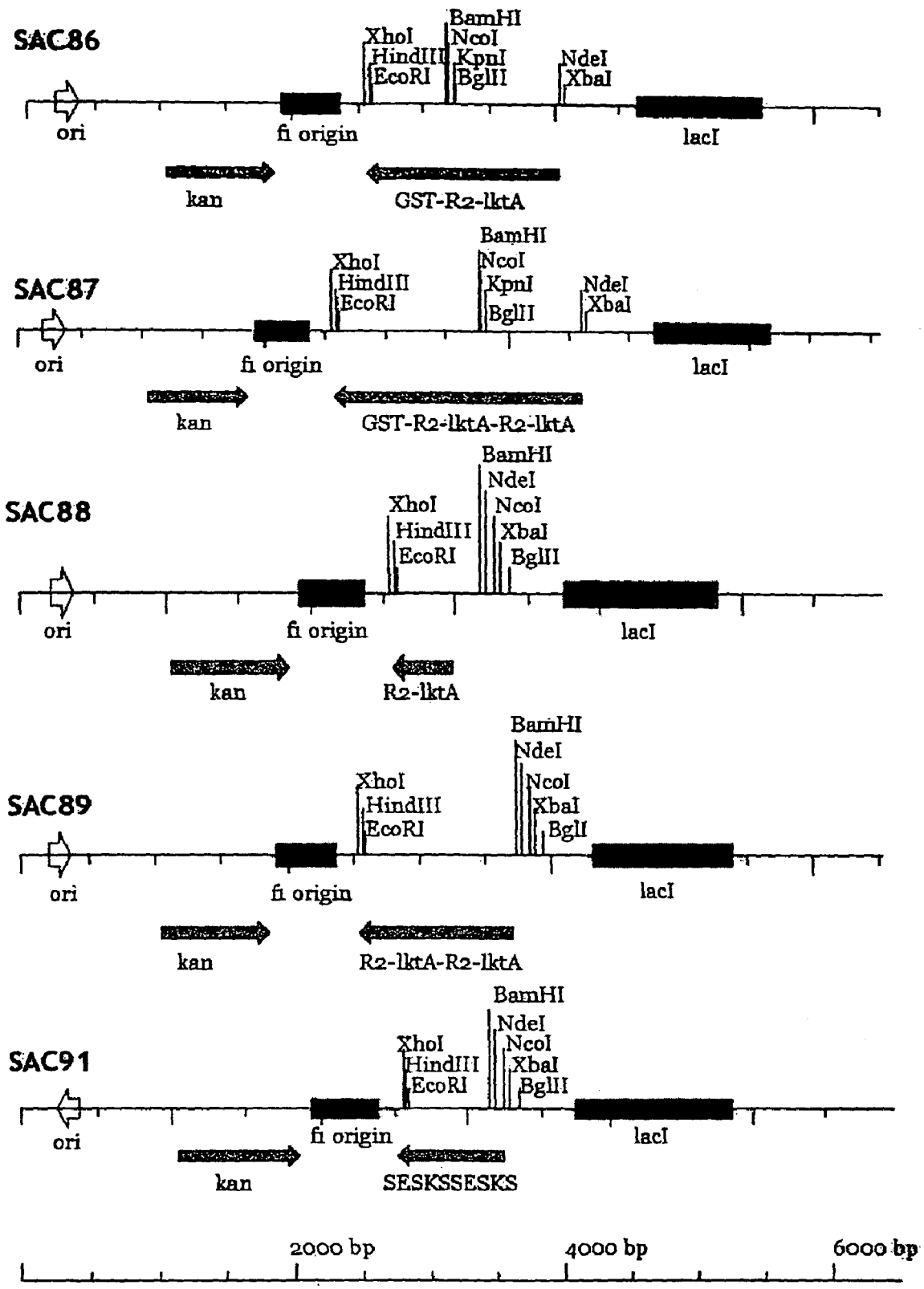
FIG. 9 A-F. Schematic representations of plasmids encoding the chimeric proteins of the invention. A, plasmid encoding SAC86; B, plasmid encoding SAC 87; C, plasmid encoding SAC88; D, plasmid encoding SAC89; E, plasmid encoding SAC91; F, linearized versions of the plasmids.

Putative antigenic regions in PlpE were identified by using the MACVECTOR™ 7.0 software that employed algorithms such as antigenic index, hydrophilicity and surface probability. However, the identification of epitopes was done with a peptide array comprising 109 overlapping 13-mer peptides that were synthesized by the chemistry described earlier. The peptides were covalently bound to derivatized cellulose membrane by the C-terminus and have a free N-terminus. Anti-PlpE hyperimmune antibodies purified by any number of the methods described earlier were used to probe the peptide array. The custom spots were stripped and probed several times. When bovine antibody against surface exposed components of PlpE that was affinity purified with intact M. haemolytica cells was used to probe the peptide array a total of 8 distinct regions (E1-8) were identified (FIG. 6). Epitope 1 (PNHPKPVLVPKTQNNL) (SEQ ID NO: 11) spans 3 peptides; epitope 2 (QNASQAQNAPQAQNAPQAQNAPQVE-NAPQAQNAPQVENAPQAE) (SEQ ID NO: 12), 11 peptides; epitope 3 (GSFDKIGSVKLNK) (SEQ ID NO: 13), 3 peptides; epitope 4 (KLGTPPKFDKVSGKKIIEE) (SEQ ID NO: 14), 6 peptides; epitope 5 (LIRRSDDLFYGYY) (SEQ ID NO: 15), 3 peptides; epitope 6 (ADKFSQYFVVYDE) (SEQ ID NO: 16), 3 peptides; epitope 7 (NISDKL-TATYRKK) (SEQ ID NO: 17), 2 peptides; and epitope 8 (PHTKEFAARISKL) (SEQ ID NO: 18). Approximately the same set of epitopes, albeit with decreasing intensities, were picked up when whole serum obtained from cows with a naturally high anti-PlpE antibody titer that were also challenged with live M haemolytica was used. The signal intensities of all of the epitopes with the exception of epitope 2 were much lesser in this blot than in the earlier. The purification of IgG from the latter serum with Protein G affinity columns did not alter the above result in that exactly the same putative epitopes were identified suggesting that IgG was the class of immunoglobulins involved in this immune response. When whole hyperimmune serum from calves immunized with rPlpE was used to probe the stripped peptide array, the same set of peptides mentioned above were identified once again confirming the binding capacity of the above indicated stretches of amino acids along PlpE. On the other hand, when sera from calves that were given live M haemolytica were used to probe the peptide array, epitope 2 was the only one that was picked up. According to the manufacturers of the custom spots, non-specific binding of the antibody-enzyme conjugate may occur to peptides that contain combinations of basic amino acids. When goat anti-bovine-HRP, the secondary antibody used in this project, was used to probe the spots, epitopes 1, 3, 4, 7, and 8 were picked up. The same sets of epitopes were identified when the array was probed with rabbit anti-bovine-HRP, showing putative epitopes 1, 3, 4, 7, and 8 were not true epitopes. In order to identify spots that would non-specifically bind bovine immunoglobulins, serum from colostrum deprived new born calf was used to probe the array. Interestingly, in addition to the putative epitopes identified by the secondary antibody-enzyme conjugates, i. e. 1, 3, 4, 7, and 8, epitopes 5 and 6 exhibited reactivity to bovine immunoglobulins. Epitope 2 was the only one that did not react to both the serum from the colostrum deprived calf and secondary antibody-enzyme conjugate showing that this epitope is the only one responsible for inducing the specific immune response when calves were either vaccinated with rPlpE or M. haemolytica.

A closer examination of epitope 2 shows that this is part of the region identified as having 8 imperfect repeats of hexapeptides (Pandher et. al., 1998). The 11 peptides (#13 through 23) identified here as epitope 2 comprise the last 4 residues of the $2^{nd}$ repeat described by Pandher et al., (1998) and the rest of the repeats i.e., repeats 3 through 8 with the exception of the $1^{st}$ hexapeptide. A feature of these 11 peptides is the lack of uniformity in their binding capacity as evidenced by the variation in their signal intensities. Peptides #15, 17, and 19 exhibit the highest signal intensities followed by #s 21 and 23. The first five residues of the N-termini of these peptides are QNAPQ (SEQ ID NO: 33) with the exception of #21 in which the first glutamine is replaced by glutamate. It is worthwhile noting that both glutamine and asparagine are positively charged, with hydrophobicity index of −0.91 and −0.92, respectively. The remaining 6 peptides in epitope 2 have proline at their N-termini instead of glutamine and this may account for their relatively lower signal intensity in the peptide array. The relatively high signal intensities exhibited by peptides 15, 17, and 19 may reflect the manner in which these epitopes are presented to the immune system under natural condition on the surfaces of M. haemolytica cells and the inherent immunogenic nature of these stretches of amino acids. The fact that epitope 2 contains a significant number of prolines at defined intervals which are usually indicators of turns, has an unusually high number of very basic residues such as glutamine, asparagine and glutamate which are hydrophilic, with high surface probability and 8 repeats are features that are usually associated with regions of protein that are associated with being immunogenic. Moreover, computer analysis of the deduced amino acid sequence of epitope 2 with algorithms such as Parker's antigenicity, Kyte/Doolittle hydrophilicity, surface probability and Chou Fasman D structure indices show that the stretch of amino acids has a moderately high antigenicity, fairly hydrophilic, contains fairly high number of amino acids with very high surface probability and is characterized by series of turns associated with helices and sheets, respectively, all of which are strong indicators of a region that is potentially highly immunogenic.

EXAMPLE 3

Construction of PlpE Chimeras 3.1 Construction of Chimeras

The importance of antibodies to the major surface-exposed and immunogenic lipoprotein PlpE in stimulating immunity to *M. haemolytica* has thus been demonstrated. In particular, it has been found that the major immunogenic epitopes of rPlpE are located in the N-terminal region of the protein, encoded (approximately) by nucleotides 231-407. In addition, promising results in stimulating immunity to *M. haemolytica* had also been obtained with the exotoxin and virulence factor leukotoxin (LKT). In particular, a "minimal" gene fragment encoding carboxy-terminal amino acids 809-939 of LKT (mLKTA) elicits a considerable leukotoxin neutralizing-antibody response in rabbits (Lainson, 1996).

The next stage of vaccine development involved the construction of chimeric proteins which included major epitopes of both of these two proteins, and tests of the ability of the chimeric proteins to elicit a protective immune response against *M. haemolytica*. Significant goals of the experiments described in this section were to develop chimeric plpe/LKTA genes, purify chimeric PldE/LKT proteins, study their immunogenicity, and develop chimeric vaccines that are efficacious against *M. haemolytica* challenge.

Five exemplary novel chimeras were constructed in which single or multiple copies of antigenic regions of rPlpE and LKT were present, with or without a glutathione-S-transferase (GST) leader sequence. The constructs contain a major surface-exposed epitope of PlpE, epitope 2, (designated "R2" in this Example, and "E2 in Examples 1-2) and mLKTA. The amino acid sequence of R2 (SEQ ID NO: 19) and the nucleic acid sequence encoding R2 (SEQ ID NO: 20) are shown in FIGS. 7A and B, respectively. The amino acid sequence of mLKTA (SEQ ID NO: 21) and the nucleic acid sequence encoding mLKTA (SEQ ID NO: 22) are shown in FIGS. 8A and B, respectively. In addition, five chimeric proteins were constructed which contained various combinations of R2 and mLKTA, separated by spacer peptides. The compositions of the five chimeras are given in Table 1 and schematic representations of the plasmids encoding the chimeras are shown in FIGS. 9A-F.

TABLE 1

Summary of the recombinant chimeric plasmids

| Plasmid Designation | Description of Insert | Name of Recombinant Protein |
|---|---|---|
| pSAC86 | G-R2-LKTA | SAC86 |
| pSAC87 | G-2(R2-LKTA) | SAC87 |
| pSAC88 | R2-LKTA | SAC88 |
| pSAC89 | 2(R2-LKTA) | SAC89 |
| pSAC91 | G-S-R2-S-LKTA-S | SAC91 |

G = GST leader peptide
R2 = immunodominant epitope of PlpE
LKTA = section of the C terminus of LKTA that includes the leukotoxin neutralizing epitope
S = GGGGS spacer peptide (SEQ ID NO: 35)

The plasmids encoding the chimeric proteins were developed and the chimeric proteins were isolated, purified and characterized as follows:

Construction of Recombinant Plasmids and Expression and Purification of Chimeric Proteins. Five chimeric proteins (SAC86, SAC87, SAC88, SAC89, & SAC91) that comprise the immunodominant epitopes of PlpE (R2) and LKT were constructed (Table 1). DNA fragments that encode for the 55 amino acids that make up the R2 region (TPNHPKPVLVP-KTQNNLQAQNVPQAQ-NASQAQNAPQAQNAPQAQNAPQVENAPQA; SEQ ID NO: 19) and the 133 amino acids that comprise the leukotoxin neutralizing epitope (SDSNLKDLTFEKVKHNLVIT-NSKKEKVTIQNWFREADFAKEVPNYKAT-KDEKIEEIIGQ NGERITSKQVDDLIAKGNGKITQDEL-SKVVDNYELLKHSKNVTNSLDKLISSVSAFTSSN DSRNVLVAPTSM; SEQ ID NO: 21) and flanking regions of LKT were amplified by polymerase chain reaction (PCR) using forward primers containing BamHI and reverse primers containing BglII. Each PCR product was cut with both BamHI and BglII and sequentially ligated into pET41 and pET28 that were digested with BamHI in the following manner. First the BamHI/BglII leukotoxin neutralizing epitope is ligated into vectors linearized with BamHI. The orientation of insertion and integrity of the constructs were confirmed by both restriction enzyme analysis and sequencing. Then these constructs were linearized with BamHI and ligated to BamHI/BglII R2 fragments. This was repeated until the desired copies of each epitope were successfully cloned in the right orientation and order. Recombinant plasmids that were derived from pET41 are pSAC86 and pSAC87 that have GST leader sequences encode for the chimeric proteins SAC86 and SAC87. Similarly, plasmids that were derived from pET28 were pSAC88 and pSAC89 and they encode for the chimeric proteins SAC88 and SAC89. The amino acid sequences of the chimeric proteins SAC86, SAC87, SAC88, SAC89 and SAC91 and the nucleotide sequences that encode them are given in FIGS. 10A-B, 11A-B, 12A-B, 13A-B and 14A-B, respectively.

Each recombinant plasmid was introduced into the *E. coli* expression host, BL21(DE3)pLysS, by transformation and recombinant chimeric proteins expressed and purified. Transformants carrying the recombinant plasmids were grown in LB broth supplemented with 30 µg of kanamycin/ml and 34 µg of chloramphenicol/ml . Expression was induced by adding isopropyl-β-D-galactopyranoside (IPTG), and cells were harvested by centrifugation at 10,000×g at 4° C., resuspended in binding buffer (6M urea, 500 mM NaCl, 20 mM Tris-HCl, 5 mM imidazole [pH 7.9]) containing protease-inhibitor cocktail III (Calbiochem, La Jolla, Calif.), and lysed in an Aminco French pressure cell (SLM Instruments, Inc., Rochester, N.Y.). Cellular debris was removed by centrifugation, and the supernatant containing the recombinant protein was clarified by filtration. Recombinant chimeric protein was purified by binding to and elution from a His•Bind® column (Novagen). Fractions containing the recombinant protein were pooled. The identity, purity, and integrity of purified proteins was determined by sodium dodecyl sulfate-polyacrylamide gel electrophoresis (SDS-PAGE) followed by Coomassie staining and Western blotting with murine anti-PlpE polyclonal ascites and murine anti-leukotoxin monoclonal antibodies.

3.2 Testing of Chimeric Proteins in a Vaccine Trials

The PlpE/LKTA chimeric proteins were tested for immunogenicity in CD-1 mice using Titermax® ™ adjuvant. The design of the experiment is presented in Table 2. Six groups of 18 mice per group were used. Groups 1-5 were further divided into 3 subgroups of 6 mice per subgroup. Mice in each subgroup were given 25, 50 or 75 µg of a chimeric protein intraperitoneally on day 0. The Group 6 mice received only adjuvant. Three mice per subgroup were bled at day 28, and the final 3 mice per subgroup were bled on day 42. Antibody responses to PlpE and LKTA were determined by ELISA

TABLE 2

Experimental design of murine chimeric protein immunization study

| Group # | Plasmid Designation | Description of Insert | Name of Recombinant Protein |
|---|---|---|---|
| 1 | pSAC86 | G-R2-LKTA | SAC86 |
| 2 | pSAC87 | G-2(R2-LKTA) | SAC87 |
| 3 | pSAC88 | R2-LKTA | SAC88 |
| 4 | pSAC89 | 2(R2-LKTA) | SAC89 |
| 5 | pSAC91 | G-S-R2-S-LKTA-S | SAC91 |
| 6 | Control | Titermax ® adjuvant only | n/a |

G = GST leader peptide
R2 = immunodominant epitope of PlpE
LktA = section of the C terminus of LktA that includes the leukotoxin neutralizing epitope
S = spacer peptide The endpoint titration data when rPlpE is used as a ligand is shown in FIG. 15A-C. (The nomenclature in the figures designates the protein and its concentration used in the vaccine, e.g. "8825" or "88-25" indicates mice vaccinated with 25 µg of SAC88.) A comparison of the immune responses to rPlpE indicates that SAC 86, 87, 88 and 89 are all highly immunogenic. However, this is not the case with SAC91, the chimera that includes spacer peptides. As can be seen, the chimeras that contain 2 copies of the epitopes from the two proteins (i.e. SAC87 and SAC89) were better immunogens, as evidenced by the high titer of the anti-rPlpE antibodies in the sera of mice that were vaccinated with these two recombinant proteins.

Antibody titers against mlktA is shown in FIG. 15D-F. As can be seen, SAC 86, SAC87, SAC88 and SAC89 elicit significantly higher antibody titers to this immunodominant epitope than does SAC91.

Figure 16:
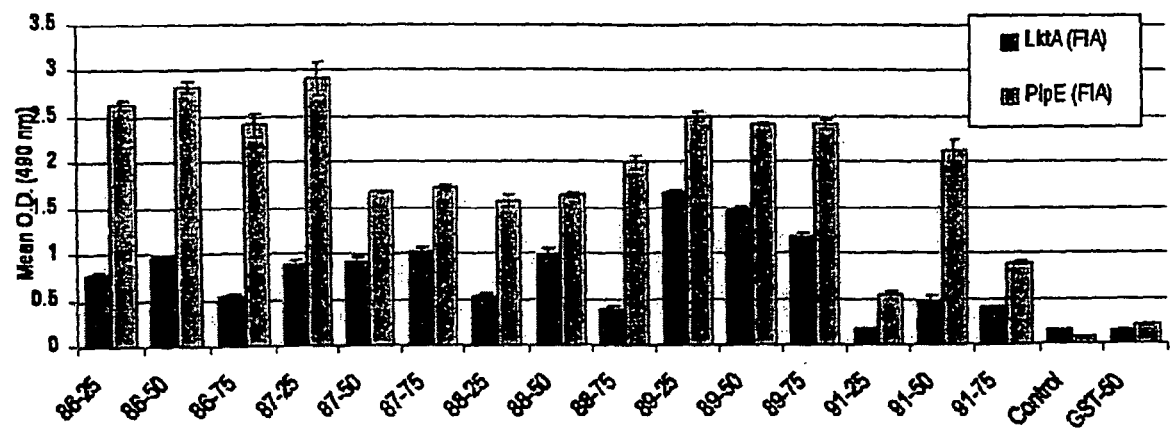
FIG. 16. Summary of antibody responses to PlpE and LKT via single dilution ELISA.

The results of a summary of antibody responses to the chimeric proteins as determined by a single dilution ELISA are presented in FIG. 16. As can be seen, according to this assay, SAC89 protein (containing two R2 and two mLKTA antigens) was the best overall antigen.

The response of mice to vaccination with the chimeric proteins was also quantified with Western blots, coupled with densitometric analysis of the bands. The results are given in FIGS. 17A and B, with FIG. 17A showing the results obtained for LKT and FIG. 17B showing the results obtained for PlpE. As can be seen, the SAC89 protein again appears to elicit the best overall response to both antigens.

Figure 18:
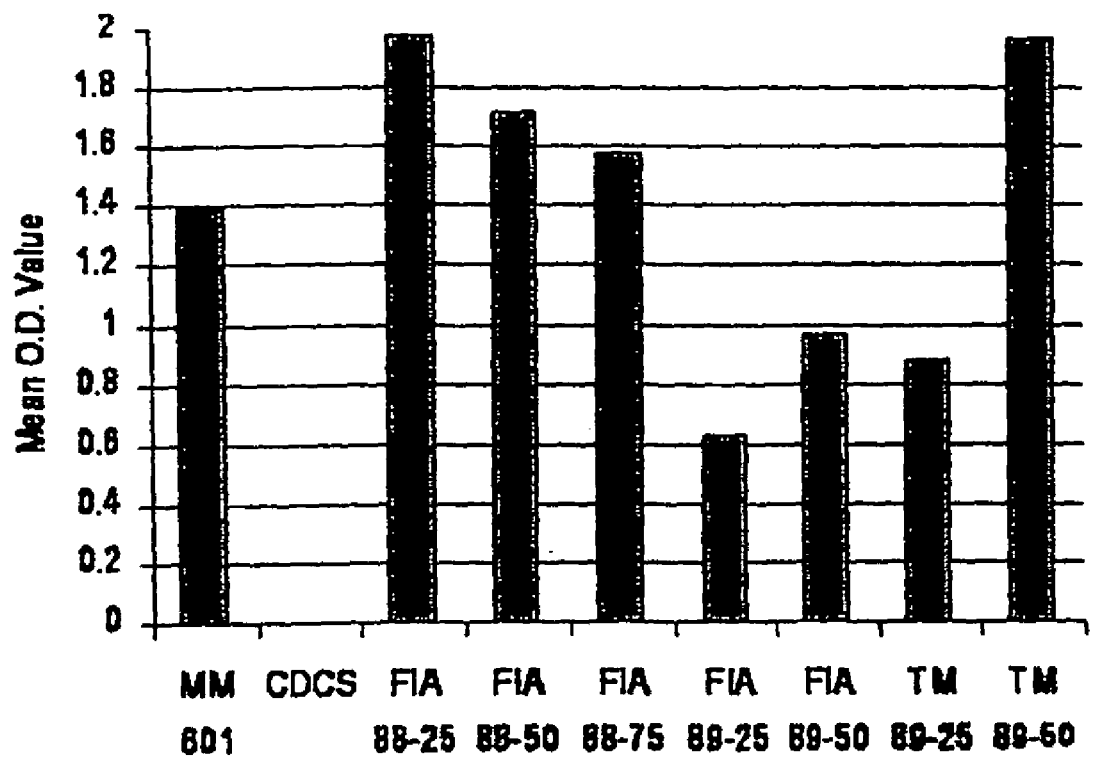
FIG. 18. LKT neutralization activity of murine anti-chimeric immune sera.

FIG. 18 depicts LKT neutralization activity of murine anti-chimeric immune sera at a dilution of 1:16 as determined by MTT assay. A colorimetric microtitration assay was adapted to quantify the cytotoxicity of LKT to bovine neutrophils used as target cells (Vega, M. V., S. K. Maheswaran, J. R. Leininger, and T. R. Ames. 1987. Adaptation of a colorimetric microtitration assay for quantifying Pasteurella haemolytica A1 leukotoxin and antileukotoxin. Am J Vet Res 48:1559-1564). The viability of LKT-treated target cells was detected by use of methylthiazole tetrazolium (MTT) assay. The MTT assay is based on measuring the activity of living cells via mitochondrial dehydrogenases that cleave the tetrazolium ring of MTT, yielding purple formazan crystals which are insoluble in aqueous solutions. The crystals are dissolved in acidified isopropanol and measured spectrophotometrically. The amount of formazan formed was quantified by use of an ELISA plate reader and is directly proportional to the number of viable target cells, thus allowing its adaptation for detecting LKT-neutralization antibody titers. The mouse sera were combined with lyophilized LKT to allow neutralization of the LKT by anti-LKT antibodies. BL-3 cells were suspended to a concentration of 2.5×106 cells/ml and 50 µl was added to each neutralization reaction. The cell mixture was incubated and the soluble MTT was added to each sample. MTT is converted by viable cells to an insoluble precipitate, which is then dissolved and read spectrophotometrically. The amount of precipitate formed relates to the amount of LKT neutralization that has occurred. LKT neutralizing mouse monoclonal antibody (MM601) was used as a positive control and colostrum-deprived calf serum (CDCS) was used as a negative control. As can be seen, LKT neutralization activity of anti-chimeric immune sera ranges from 45% to 142% of that of MM601.

Figure 19:
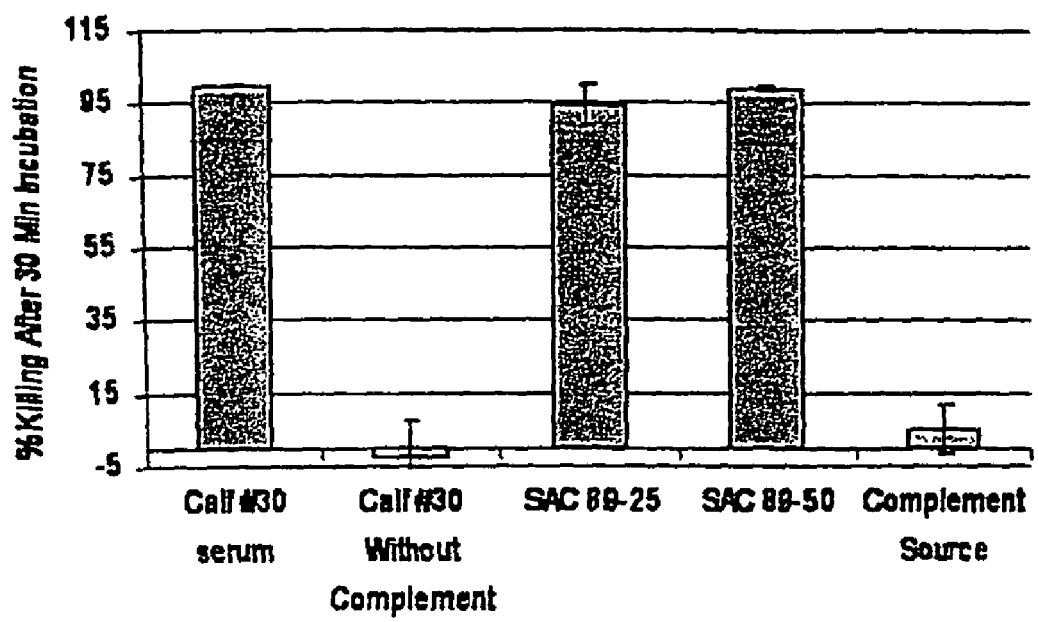
FIG. 19. Bactericidal activity of murine anti-SAC89 hyper-immune sera compared to anti-PlpE hyper-immune calf serum.

FIG. 19 depicts bactericidal activity of murine anti-SAC-89 hyper-immune sera obtained as the result of administering either 25 µg of SAC89 (89-25) or 50 µg of SAC89 (89-50). Tests were carried out in the presence of a suitable source of complement. Tests were carried out in the presence of a suitable source of complement. Complement-mediated killing assay was done as we have previously described (Ayalew, S., A. W. Confer, and E. R. Blackwood. 2004. Characterization of immunodominant and potentially protective epitopes of Mannheimia haemolytica serotype 1 outer membrane lipoprotein PlpE. Infect Immun 72:7265-7274.). Briefly, M. haemolytica cells were grown in BHI broth and decapsulated in 1×PBS at 41° C. The cells were resuspended to an $O.D._{600}=0.500$ and then diluted to 1:1000 in PBS for use in the assay. The mouse sera were heat treated at 56° C. to inactivate existing complement and used as the antibody sources. Colostrum-deprived calf serum was used as the source of complement in the assay. The antibodies, bovine complement, and decapsulated M. haemolytica cells were mixed and plated on BHIA Blood plates at $T_0$ and $T_{30}$ after incubation at 37° C. Growth was determined by counting the number of colonies present after 15-16 hours of incubation at 37° C. and 5% $CO_2$ and the percent killing was calculated with the formula: $[(T_0 \text{ growth} - T_{30} \text{ growth})/T_0 \text{ growth}] \times 100\%$ The results showed that the serum bactericidal activity of mouse anti-SAC89 hyper-immune sera is as potent as serum from a calf that was vaccinated with intact rPlpE.

EXAMPLE 4

Vaccination With SAC89 and Challenge With Mannheimia haemolytica Experimental design and results. Fifteen recently weaned Angus cross steers were purchased. Eight were vaccinated subcutaneously with PBS in Emulsigen-P adjuvant on day 0, whereas 7 received 100 µg of SAC89 plus adjuvant subcutaneously in the neck. The vaccine was repeated on day 28. Antibody responses against SAC89, leukotoxin, recombinant PlpE, and whole bacterial cells were significantly increased by day 14 after vaccination (FIG. 20 A-D). A decline in antibodies followed with a significantly higher response after revaccination on day 28. During the course of the study, calf #48 caught its head in a feed bunk and broke its neck. It was thus removed from the study.

On day 42, cattle were challenged transthoracically with 5×109 CFU of live, virulent Mannheinia haemolytica A1 Oklahoma strain (Panciera & Corstvet, Am J Vet Res. 1984 December; 45 (12:2532-7). Calf #25 died within 3 days after challenge due to severe pneumonia and terminal septicemia and was given the maximum score of 20 (Panciera et al. Am J Vet Res 1984 December; 45 (12);2538-42). Four days after challenge, cattle were humanely killed and lungs evaluated for lesion scores on a 20 point scale (0 being no lesion and 20 being maximum). There was a significant reduction (69.9%, p <0.02) in lesion scores for SAC89 vaccinates compared to PBS/Adjuvant vaccinates (Table 3).

TABLE 3

Lesion scores after vaccination with SAC89 or PBS

| Calf No. | Vaccine | Lesion Score |
|---|---|---|
| 8 | PBS/ADJ | 1.5 |
| 21 | PBS/ADJ | 7.5 |
| 22 | PBS/ADJ | 7.5 |
| 25 | PBS/ADJ | 20 |
| 29 | PBS/ADJ | 13 |
| 31 | PBS/ADJ | 8.5 |
| 41 | PBS/ADJ | 5 |
| 42 | PBS/ADJ | 1.5 |
| 48 | PBS/ADJ | Deceased* |
| Mean ± SD | | 8.06 ± 6.13 |
| 3 | SAC89/ADJ | 1.5 |
| 7 | SAC89/ADJ | 1.5 |
| 12 | SAC89/ADJ | 0 |
| 23 | SAC89/ADJ | 2 |
| 30 | SAC89/ADJ | 2 |
| 32 | SAC89/ADJ | 5.5 |
| 39 | SAC89/ADJ | 4.5 |
| Mean ± SD | | 2.43 ± 1.9 |
| | | (69.9% reduction in lesion scores) |

*Calf died from an accident and was removed from the study.
P < 0.02 between vaccinates and controls This example shows that vaccination of cattle with a recombinant chimeric protein comprising PlpE-LKT of *M. haemolytica* provides significant protection against challenge with virulent *M. Haemolytica*. In addition, the vaccine stimulates antibodies to M. haemolytica LKT, whole cells, outer membrane lipoprotein PlpE and to the chimeric protein itself.

Accordingly, it can be appreciated that subunits derived from PlpE, and especially epitope 2 (i.e. R2), are useful as well in the inventive vaccine compositions and methodologies. The inclusion of such region(s) enhances the host immune response directed against relevant immunoprotective epitopes. It accordingly can be appreciated that the inventive vaccines utilize as distinct antigenic components rPlpE or subunits thereof capable of eliciting an antibody or other immune response against *M. haemolytica*. As a result, the invention encompasses proteins which may be the full length antigen, antigen fragment, antigen derivative or a fusion product of such antigen, antigen fragment or antigen derivative with another protein. In particular, chimeric proteins comprising antigenic regions of rPlpE and LKT are effective in eliciting a protective immune response against *M. haemolytica*. Proteins included within the present invention include those depicted in the Sequence Listing as well as mutants of said sequences capable of eliciting an antibody or other immune response which recognizes an epitope(s) of such amino acid sequences. In general, the polypeptides that represent the proteins of the invention will have at least from about 60 to 70% identity with the sequences presented herein, and preferably about 70 to about 80% identity, and more preferably about 80 to 90% identity, and most preferably about 90-95 or 95-100% identity.

In addition, the chimeric proteins of the invention may also include a leader sequence. In one embodiment, the leader sequence is glutathione-S-transferase (GST), the sequence of which is known and readily available (see, for example, U.S. Pat. No. 6,368,584, the contents of which is hereby incorporated by reference). However, those of skill in the art will recognize that other leader sequences exist which are also suitable for use in the invention.

In addition, other short sequences may serve as "spacer+ peptides, for example, between R2 peptide sequences in a polypeptide that comprises more than one R2 sequence, and/ or between R2 peptide sequences in a polypeptide that comprises one or more of R2 or mLKT, or both. In one embodiment, the spacer peptide is Arg-Ser (i.e. "RS"). However, those of skill in the art will recognize that other spacer peptides may also be used in the practice of the invention, including but not limited to Gly-Gly-Gly-Ser (i.e. GGGS, SEQ ID NO: 34), and others, so long as the spacer peptides allow exposure of the antigenic epitopes to the immune system a manner that results in an immune response.

The nucleotide sequences used to generate the antigens may be inserted into any of a wide variety of expression vectors by a variety of procedures. Such procedures and others are deemed to be known by those skilled in the art. Suitable vectors include chromosomal, nonchromosomal and synthetic DNA sequences; e. g., derivatives of SV40; bacterial plasmids; phage DNAs ; yeast plasmids; vectors derived from combinations of plasmids and phage DNAs, viral DNA such as baculovirus, vaccinia, adenovirus, fowl pox virus, pseudorabies, etc. The appropriate DNA sequence must be operatively linked in the vector to an appropriate expression control sequence(s) (promoter) to direct mRNA synthesis. As representative examples of such promoters, there may be mentioned LTR or SV40 promoter, the *E. coli* lac or trp, the phage lambda PL promoter and other promoters known to control expression of genes in prokaryotic and eukaryotic cells or their viruses. The expression vector also includes a non-coding sequence for a ribosome binding site for translation initiation and a transcription terminator. The vector may also include appropriate sequences for amplifying expression.

The vector containing an appropriate sequence, as well as an appropriate promoter or control sequence, may be employed to transform an appropriate host to permit the host to express the protein. Examples of host organisms and cells include bacterial strains (e. g., *E. coli, Pseudomonas, Bacillus, Salmonella*, etc.), fungi (e. g., yeasts and other fungi), animal or plant hosts (e.g., mouse, swine or animal and human tissue cells). The selection of the host is deemed to be within the scope of those skilled in the art.

As previously mentioned, it is also understood that the appropriate sequence present in the vector when introduced into a host may express part or only a portion of the protein which is encoded within the noted terminology, it being sufficient that the expressed protein be capable of eliciting an antibody or other immune response which recognizes an epitope(s) of the listed amino acid sequences.

The isolated polypeptides expressed by the host transformed by the vector may be harvested by methods which will occur to those skilled in the art and used in a vaccine for providing an enhanced immune response against infection with *M. haemolytica*. Vaccine preparation is easily accomplished using well known methods and techniques. An enhanced immune response is manifest by protection against infection or a decrease in severity of infection, which may be reflected in body temperature and antibody titers as described above.

The host expressing the antigen may itself be used to deliver antigen to non-human animals, by introducing killed or viable host cells that are capable of propagating in the animal. Direct incorporation of the nucleotide sequences into host cells may also be used to introduce the sequences into animal cells for expression of antigen in vivo.

Vaccine preparations are combined with physiologically acceptable carriers to form vaccines. The carrier employed in conjunction with vaccine may be any one of a wide variety of carriers. As representative examples of suitable carriers, there may be mentioned mineral oil, synthetic polymers, etc. Carriers for vaccines are well known in the art and the selection of a suitable carrier is deemed to be within the scope of those skilled in the art. The selection of a suitable carrier is also dependent upon the manner in which the vaccine is to be administered. The preferred physiologically acceptable carrier is an adjuvant. Preferably, the inventive vaccine formulation is set to contain about 10-100, and preferably about 100, micrograms of recombinant antigens in commercially available adjuvant (Pfizer). Similar quantities of recombinant antigens would be used if added to another commercial vaccine formulation.

Examples of adjuvants that may be used in the practice of the invention include but are not limited to: aluminum hydroxide gel-based adjuvants, saponin-based adjuvants, block co-polymer-based adjuvants, water-in-oil adjuvants, and oil-in-water adjuvants. Specific examples include but are not limited to Freund's incomplete adjuvant, TiterMax®, Emulsigen®-P, Xtend II, Xtend SP, SUPERIMM®, and RIBI adjuvant.

The vaccines may be administered by a variety of routes including intravenously, intraperitoneally, intramuscularly, and subcutaneously. The preferred route of administration is subcutaneous. Alternatively, the vaccine may be administered intranasally or orally. The vaccine can be administered in a single dose or multiple doses until a protective effect is achieved.

Those of skill in the art will further recognize that in order to function as a "vaccine", inoculation with a protein of the invention (e.g. a chimeric protein) may, on the one hand, offer full protection from the development of symptoms associated with infection by M. haemolytica (i.e. so-called symptoms of "shipping fever"). However, a vaccine preparation can be valuable even if symptoms are not totally prevented, but are merely attenuated. Further, the vaccine preparation may be used prophylactically prior to suspected exposure to the etiological agent of the disease, or after exposure, or even after some symptoms of disease have appeared. Benefit from the immune stimulating effects of the vaccine preparation that is administered may accrue even after the onset of infection.

The vaccines of the invention may be administered alone as the sole agent for combating M. haemolytica infection. Alternatively, the vaccine preparations may be administered in concert with other agents such as vaccine preparations utilizing other M. haemolytica proteins or antigens, several commercial varieties of which are known.

According to the invention, chimeric proteins which include one or more immunodominant epitopes of recombinant PlpE in combination with one or more immunodominant epitopes of LKT, are provided as vaccinating agents. Those of skill in the art will recognize that several terms are used in the art to describe peptide and/or polypeptide sequences that elicit an immune response, and that there is sometimes overlap or inconsistency within the art with respect to the categorization of such sequences. Herein, the term "immunodominant epitope" or "immunodominant region" is intended to refer to regions (i.e. segments or portions) of a protein from a pathogenic organism that, when administered to a mammal, are capable of inducing a protective immune response to the organism in the mammal. Generally, but not always, such immundominant regions or epitopes are highly immunogenic when tested according to methods that are known to those of skill in the art, such as those described herein.

In a preferred embodiment of the invention, the exemplary immunodominant region or epitope of PlpE that is utilized is R2 as represented by SEQ ID NO: 19, and the exemplary immunodominant region or epitope of LKT is mLKT as represented by SEQ ID NO: 21. In addition, those of skill in the art will recognize that several modifications of these sequences can be made for any of several purposes, without compromising the ability of the chimeric protein to elicit a suitable immune response. For example, conservative amino acid substitutions can be tolerated. Conservative amino acid substitution can be defined as recognized by those of skill in the art, for example, according to the BLOSUM62 matrix, described by Henikoff and Henikoff (S. Hemikoff and J. G. Henikoff, Proc. Natl. Acad. Sci. USA 89, 10915-10919, 1992). In addition, the deletion of a small number (e.g. approximately 1-10) amino acids from the amino or carboxy terminus or within the sequence, or the substitution of various modified or non-natural amino acids, addition of histidine tags, etc. may also be tolerated without compromising the ability of the immunodominant region or epitope to function in the practice of the present invention. Such modifications may be carried out for any of a variety of purposes, including but not limited to increase or decrease solubility of the polypeptide, to prevent or aid digestion by proteases, to facilitate isolation and purification of the protein (polypeptide), etc. Further, various labels may be included to facilitate tracking of the protein (e.g. introduction of a tryptophan residue, or introduction of a chemical label). In general, polypeptides that are encompassed by the invention will have at least from about 60 to 70% identity with the sequences presented herein, and preferably about 70 to about 80% identity, and more preferably about 80 to 90% identity, and most preferably about 90-95 or even about 95-100% identity, e.g. to R2, or to mLKTA individually. All such sequence variants are intended to be encompassed by the invention, so long as the resultant peptide sequence retains the activity of the parent peptide sequence. Those of skill in the art are well acquainted with methods by which one can test and compare the immunogenicity of different peptides/polypeptides and their effectiveness in eliciting an immune response, and their ability to provide protection to challenge with a disease-causing entity. Exemplary methods are fully described in the Examples section of this application.

In some embodiments, the chimeric protein contains multiple copies of the immunodominant epitopes. In one embodiment, the chimera contains two copies each of R2 and mLKTA. However, this need not be the case. Higher numbers of copies are also contemplated (e.g. 3 or even many more). Any number of copies may be utilized, so long as the construct that encodes the chimera and the chimera itself are able to be successfully manipulated and processed in the laboratory and during vaccine preparation. Further, the number of copies of each moiety (R2 and mLKTA) need not be equal, i.e. a chimera may contain one copy of R2 and two or more copies of mLKTA, or vice versa. In addition, one or more immunodominant epitopes from other species or strains can also be incorporated into the chimera, e.g. from other M. haemolytica.

In addition, the arrangement (i.e. order or position) of the immunodominant regions within the chimeric protein may vary. For example, the protein may contain two R2 regions in tandem, followed by two mLKTA regions in tandem. Alternatively, a protein may contain alternate regions, e.g. R2-mLKTA-R2-mLKTA, etc. Any such combination is considered to be within the scope of the invention, so long as the resulting chimeric protein elicits a suitable and useful immune response to M. haemolytica, e.g. a sufficient response to prevent or attenuate symptoms of disease that would likely occur in the vaccinated mammal, if the mammal had not been vaccinated by a preparation containing the chimeric protein.

Likewise, while exemplary DNA acid sequences that encoding chimeric proteins are presented herein, those of skill in the art will recognize that the nucleic acids of the invention are not limited to those specific sequences, or even to DNA. RNA encoding the chimeric proteins is also within the scope of the invention, as are modifications to the encoding sequences that can be tolerated without vitiating the efficacy of the polypeptide that is produced. For example, due to the redundancy of the genetic code, many sequences other than those that are presented may be used in the practice of the invention. Other variants of the nucleic acid sequences may be introduced, for example, in order to stabilize the nucleic acid, to facilitate isolation or tracking of the DNA (e.g. various labels), etc. In general, nucleic acid sequences that are included in the present invention will be about 60 to 70% homologous to the sequences presented herein, and preferably about 70 to about 80% homologous, and more preferably about 80 to 90% homologous, and most preferably about 90-95 or 95-100% homologous, e.g. to R2, or to mLKTA encoding sequences.

In addition to the administration of a proteinaceous vaccine preparation, the invention also contemplates administration of a nucleic acid encoding the antigenic protein. In this embodiment, the protein (e.g. a chimeric protein) is translated within the vaccinated host. Those of skill in the art are aware of the many systems for delivery of nucleic acid (e.g. DNA) vaccines, including liposomal preparations, various viral vectors, (e.g. adenovirus, hepatitis, etc.), and the like.

In view of the above, it will be seen that the several objectives of the invention are achieved and other advantageous results attained. As various changes could be made in the above sequences, antigens, etc. without departing from the scope of the invention, it is intended that all matter contained in the above description or shown in the accompanying drawings shall be interpreted as illustrative and not in a limiting sense.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

We claim:

1. A purified chimeric protein comprising one or more copies of an isolated N-terminal immunodominant epitope of recombinant *Mannheimia haemolytica* S1 outer membrane lipoprotein (rPlpE) and one ore more copies of an isolated immunodominant epitope of recombinant *Mannheimia haemolytica* leukotoxin (LKT), wherein the immunodominant epitope of the LKT is mLKT A having the amino acid sequence as set forth in SEQ ID No: 21.

2. The chimeric protein of claim 1, wherein said immunodominant epitope of said rPlpE is R2 epitope having the amino acid sequence as set forth in SEQ ID No: 19.

3. The chimeric protein of claim 1, wherein said chimeric protein further comprises a leader sequence.

4. The chimeric protein of claim 3, wherein said leader sequence is glutathione-S-transferase leader sequence.

5. The chimeric protein of claim 1, wherein said chimeric protein further comprises one or more spacer peptides.

6. The chimeric protein of claim 1, wherein said chimeric protein comprises two copies of said rPlpE and two copies of said LKT.

7. A vaccine preparation comprising at least one purified chimeric protein comprising one ore more copies of an isolated N-terminal immunodominant epitope of recombinant *Mannheimia haemolytica* S1 outer membrane lipoprotein (rPlpE) and one or more copies of an isolated immunodominant epitope of recombinant *Mannheimia haemolytica* leukotoxin (LKT), wherein the immunodominant epitope of the LKT is mLKT A having the amino acid sequence as set forth in SEQ ID NO: 21, and a physiologically compatible carrier.

8. The vaccine preparation of claim 7, wherein said immunodominant epitope of said rPlpE is R2 epitope having the amino acid sequence as set forth in SEQ ID NO: 19.

9. The vaccine preparation of claim 7, wherein said at least one chimeric protein further comprises a leader sequence.

10. The vaccine preparation of claim 9, wherein said leader sequence is glutathione-S-transferase leader sequence.

11. The vaccine preparation of claim 7, wherein said at least one chimeric protein further comprises one or more spacer peptides.

12. The vaccine preparation of claim 7, wherein said at least one chimeric protein comprises two copies of said rPlpE and two copies of said LKT.

13. The vaccine preparation of claim 7 further comprising an adjuvant.

\* \* \* \* \*